(12) United States Patent
Feldman et al.

(10) Patent No.: US 9,482,513 B2
(45) Date of Patent: Nov. 1, 2016

(54) APPARATUS AND METHODS FOR OPTICAL COHERENCE TOMOGRAPHY AND TWO-PHOTON LUMINESCENCE IMAGING

(71) Applicant: RESEARCH DEVELOPMENT FOUNDATION, Carson City, NV (US)

(72) Inventors: Marc Feldman, San Antonio, TX (US); Thomas Milner, Austin, TX (US); Tianyi Wang, Austin, TX (US); Jennifer Phipps, San Antonio, TX (US)

(73) Assignee: Research Development Foundation, Carson City, NV (US)

( * ) Notice: Subject to any disclaimer, the term of this patent is extended or adjusted under 35 U.S.C. 154(b) by 0 days.

(21) Appl. No.: 14/212,756

(22) Filed: Mar. 14, 2014

(65) Prior Publication Data

US 2014/0268168 A1    Sep. 18, 2014

Related U.S. Application Data

(60) Provisional application No. 61/785,030, filed on Mar. 14, 2013.

(51) Int. Cl.
*G01B 9/02* (2006.01)
*A61B 5/00* (2006.01)

(52) U.S. Cl.
CPC ......... *G01B 9/02091* (2013.01); *A61B 5/0066* (2013.01); *G01B 9/02007* (2013.01); *G01B 9/02014* (2013.01); *G01B 2290/70* (2013.01)

(58) Field of Classification Search
CPC .............. G01B 9/02091; G01B 9/02007
USPC .................................................. 356/479
See application file for complete search history.

(56) References Cited

U.S. PATENT DOCUMENTS

| | | |
|---|---|---|
| 6,249,630 B1 | 6/2001 | Stock et al. |
| 2002/0101593 A1* | 8/2002 | Yang et al. ............... 356/484 |
| 2005/0002028 A1 | 1/2005 | Kasapi et al. |
| 2005/0119552 A1 | 6/2005 | Hochman |
| 2005/0171433 A1* | 8/2005 | Boppart et al. ............ 600/473 |
| 2005/0265405 A1 | 12/2005 | Mannstadt et al. |
| 2007/0081166 A1* | 4/2007 | Brown ............... A61B 3/1005 356/479 |
| 2008/0117424 A1 | 5/2008 | Teramura et al. |
| 2009/0021724 A1* | 1/2009 | Mahadevan-Jansen et al. ............... 356/73 |
| 2009/0021746 A1* | 1/2009 | Toida et al. ............... 356/484 |

(Continued)

FOREIGN PATENT DOCUMENTS

WO    WO 2006/004743    1/2006

OTHER PUBLICATIONS

Albota et al., "Two-photon fluorescence excitation cross sections of biomolecular probes from 690 to 960 nm", *Appl. Opt.*, 37(31): 7352-7356, 1998.

(Continued)

*Primary Examiner* — Jonathan Hansen
(74) *Attorney, Agent, or Firm* — Parker Highlander PLLC

(57) ABSTRACT

Exemplary embodiments of the present disclosure include a combined catheter-based optical coherence tomography-two-photon luminescence (OCT-TPL) imaging system. Exemplary embodiments further include methods to detect, and further characterize the distribution of cellular components (e.g., macrophage, collagen/elastin fiber, lipid droplet) in thin-cap fibroatheromas with high spatial resolution in vivo.

22 Claims, 21 Drawing Sheets
(6 of 21 Drawing Sheet(s) Filed in Color)

(56) References Cited

U.S. PATENT DOCUMENTS

| | | | |
|---|---|---|---|
| 2009/0185191 | A1 | 7/2009 | Boppart et al. |
| 2010/0286674 | A1 | 11/2010 | Ben-Yakar et al. |
| 2011/0032479 | A1 | 2/2011 | Utsunomiya |
| 2011/0300490 | A1 | 12/2011 | Rachet et al. |
| 2012/0140301 | A1* | 6/2012 | Xu .................. G02B 23/243 359/198.1 |
| 2012/0203114 | A1 | 8/2012 | Bechtel et al. |

OTHER PUBLICATIONS

Bouhelier et al., "Surface plasmon characteristics of tunable photoluminescence in single gold nanorods", *Phys. Rev. Lett.*, 95(26): 2674051-2674054, 2005.

Boulesteix et al., "Micrometer scale ex vivo multiphoton imaging of unstained arterial wall structure", *Cytometry Part A*, 69A: 20-26, 2006.

Boyd et al., "Photoinduced luminescence from the noble metals and its enhancement on roughened surfaces", *Phys. Rev. B*, 33(12): 7923-7936, 1986.

Castellana et al., "Longitudinal surface plasmon resonance based gold nanorod biosensors for mass spectrometry", *Langmuir*, 26(8): 6066-6070, 2010.

Chen et al., "In situ real-time investigation of cancer cell photothermolysis mediated by excited gold nanorod surface plasmons", *Biomaterials*, 31(14): 4104-4112, 2010.

El-Sayed, "Some interesting properties of metals confined in time and nanometer space of different shapes", *Acc. Chem. Res.*, 34(4): 257-264, 2001.

Eustis and El-Sayed, "Aspect ratio dependence of the enhanced fluorescence intensity of gold nanorods: experimental and simulation study," *J Phys. Chem. B*, 109(34): 16350-16356, 2005.

Fang et al., "Plasmon emission quantum yield of single gold nanorods as a function of aspect ratio", *ACS Nano*, 6(8): 7177-7184, 2012.

Fu and Gu, "Double-clad photonic crystal fiber coupler for compact nonlinear optical microscopy imaging", *Opt Lett.* 31: 1471-1473, 2006.

Fu et al., "Nonlinear optical endoscopy based on a double-clad photonic crystal fiber and a MEMS mirror", *Opt Exp.*, 14: 1027-1032, 2006.

Gans, "Form of ultramicroscopic particles of silver", *Ann. Phys.* 47(10): 270-284, 1915. (German).

Hauck et al., "Assessing the effect of surface chemistry on gold nanorod uptake, toxicity, and gene expression in mammalian cells", *Small*, 4(1): 153-159, 2008.

Huang et al., "Gold nanorods: from synthesis and properties to biological and biomedical applications," *Adv. Mater.*, 21(48): 4880-4910, 2009.

Hummel, *Electronic Properties of Materials*, 37-61, 4th ed. (Springer, New York, 2011).

Imura et al., "Near-field two-photon-induced photoluminescence from single gold nanorods and imaging of plasmon modes", *J. Phys. Chem. B*, 109(27): 13214-13220, 2005.

Jain et al., "Noble metals on the nanoscale: optical and photothermal properties and some applications in imaging, sensing, biology, and medicine", *Acc. Chem. Res.*, 41(12): 1578-1586, 2008.

Jain et al., "Review of some interesting surface plasmon resonance-enhanced properties of noble metal nanoparticles and their applications to biosystems", *Plasmonics*, 2(3): 107-118, 2007.

Janát-Amsbury et al., "Geometry and surface characteristics of gold nanoparticles influence their biodistribution and uptake by macrophages", *Eur. J. Pharm. Biopharm.*, 77(3): 417-423 2011.

Ji et al., "Bifunctional Gold Nanoshells with a Superparamagnetic Iron Oxide-Silica Core Suitable for Both MR Imaging and Photothermal Therapy", *J. Phys. Chem. C*, 111(17): 6245-6251, 2007.

Kim et al., "Fiber-optic spectral polarimeter using a broadband swept laser source," *Optics Communications*, 249: 351-356, 2005.

Lal et al., "Nanoshell-enabled photothermal cancer therapy: impending clinical impact", *Acc. Chem. Res.*, 41(12): 1842-1851, 2008.

Le et al., "Label-free molecular imaging of atherosclerotic lesions using multimodal nonlinear optical microscopy", *J Biomed Opt.*, 12(5): 0540071-05400710, 2007.

Lee and El-Sayed, "Dependence of the enhanced optical scattering efficiency relative to that of absorption for gold metal nanorods on aspect ratio, size, end-cap shape and medium refractive index," *J. Phys. Chem. B*, 109(43): 20331-20338, 2005.

Lilledahl et al., "Characterization of vulnerable plaques by multiphoton microscopy", *J Biomed Opt.*, 12(4): 0440051-04400512, 2007.

Link et al., "Laser-induced shape changes of colloidal gold nanorods using femtosecond and nanosecond laser pulses", *J. Phys. Chem. B*, 104(26): 6152-6163, 2000.

Link et al., "Simulation of the optical absorption spectra of gold nanorods as a function of their aspect ratio and the effect of the medium dielectric constant", *J. Phys. Chem. B*, 106(16): 3073-3077, 1999.

Liu et al., "Multiphoton microscopy system with a compact fiber-based femtosecond-pulse laser and handheld probe", *J Biophoton.*, 4: 34-39, 2011.

Longmire et al., "Clearance properties of nano-sized particles and molecules as imaging agents: considerations and caveats", *Nanomedicine (Lond)*, 3(5): 703-717, 2008.

Ma et al., "Small multifunctional nanoclusters (nanoroses) for targeted cellular imaging and therapy", *ACS Nano*, 3(9): 2686-2696, 2009.

Mohamed et al., "The 'lightning' gold nanorods: fluorescence enhancement of over a million compared to the gold metal", *Chem. Phys. Lett.*, 317(6): 517-523, 2000.

Mooradian, "Photoluminescence of metals", *Phys. Rev. Lett.*, 22(5): 185-187, 1969.

Nagesha et al., "In vitro imaging of embryonic stem cells using multiphoton luminescence of gold nanoparticles", *Int. J. Nanomedicine*, 2(4): 813-819, 2007.

Ni et al., "Tailoring longitudinal surface plasmon wavelengths, scattering and absorption cross sections of gold nanorods," *ACS Nano*, 2(4): 677-686, 2008.

Niidome et al., "PEG-modified gold nanorods with a stealth character for in vivo applications", *J. Control Release*, 114(3): 343-347, 2006.

Ohulchanskyy et al., "High-resolution light microscopy using luminescent nanoparticles", *WIREs Nanomed. Nanobiotechnol.*, 2(2): 162-175, 2010.

Okamoto and Imura, "Near-field imaging of optical field and plasmon wavefunctions in metal nanoparticles," *J. Mater. Chem.*, 16(40): 3920-3928, 2006.

Park et al., "Two-photon-induced photoluminescence imaging of tumors using near-infrared excited gold nanoshells", *Opt Exp.* 16(3): 1590-1599, 2008.

PCT International Search Report and Written Opinion issued in International Application No. PCT/US2014/028403, mailed Sep. 10, 2014.

Ryu et al., "Optical coherence tomography implemented by photonic crystal fiber", *Opt Quant Electron.*, 37(13-15): 1191-1198, 2005.

Shukla et al., "Biocompatibility of gold nanoparticles and their endocytotic fate inside the cellular compartment: a microscopic overview", *Langmuir*, 21(23): 10644-10654, 2005.

Skrabalak et al., "Gold nanocages for cancer detection and treatment", *Nanomedicine (Lond)*, 2(5): 657-668, 2007.

Sönnichsen and Alivisatos, "Gold nanorods as novel nonbleaching plasmon-based orientation sensors for polarized single-particle microscopy", *Nano Lett.*, 5(2): 301-304, 2005.

Sönnichsen et al., "Drastic reduction of plasmon damping in gold nanorods", *Phys. Rev. Lett.*, 88: 077402-077405, 2002.

Tong et al., "Gold nanorods as contrast agents for biological imaging: optical properties, surface conjugation and photothermal effects," *Photochem. Photobiol.*, 85(1): 21-32, 2009.

(56) References Cited

OTHER PUBLICATIONS van Zandvoort et al., "Two-photon microscopy for imaging of the (atherosclerotic) vascular wall: a proof of concept study", *J Vasc Res.*, 41: 54-63, 2004.

Verma and Sekhon, "Influence of aspect ratio and surrounding medium on localized surface plasmon resonance (LSPR) of gold nanorod", *J. Optics.*, 41(2): 89-93, 2012.

Wang et al., "Combined two-photon luminescence microscopy and OCT for macrophage detection in the hypercholesterolemic rabbit aorta using plasmonic gold nanorose", *Lasers Surg. Med.*, 44(1): 49-59, 2012.

Wang et al., "Dual-wavelength multi-frequency photothermal wave imaging combined with OCT for macrophage and lipid detection in atherosclerotic plaques", *J Biomed Opt.*, 17(3): 0360091-03600910, 2012.

Wang et al., "In vitro and in vivo two-photon luminescence imaging of single gold nanorods", *Proc. Natl. Acad. Sci. USA*, 102(44): 15752-15756, 2005.

Wang et al., "Near-IR luminescence of monolayer-protected metal clusters", *J. Am. Chem. Soc.*, 127(3): 812-813, 2005.

Wilcoxon et al., "Photoluminescence from nanosize gold clusters", *J. Chem. Phys.*, 108(21): 9137-9143, 1998.

Winsemius et al., "Splitting of the interband absorption edge in Au", *Phys. Rev. B*, 12(10): 4570-4572, 1975.

Wu et al., "Scanning fiber-optic nonlinear endomicroscopy with miniature aspherical compound lens and multimode fiber collector", *Opt Lett.*, 34: 953-955, 2009.

Xu and Webb, "Measurement of two-photon excitation cross sections of molecular fluorophores with data from 690 to 1050 nm", *JOSA B*, 13(3): 481-491, 1996.

Xue and Fujimoto, "Ultrahigh resolution optical coherence tomography with femtosecond Ti:sapphire laser and photonic crystal fiber", *Chinese Science Bulletin*, 53(13): 1963-1966, 2008.

Zhang et al., "Gold nanorods for fluorescence lifetime imaging in biology", *J. Biomed. Opt.*, 15(2): 0205041-0205043, 2010.

Zheng et al., "Highly fluorescent, water-soluble, size-tunable gold quantum dots", *Phys. Rev. Lett.*, 93(7): 077402-077405, 2004.

Zoumi et al., "Imaging coronary artery microstructure using secondharmonic and two-photon photon fluorescence microscopy", *Biophys J.*, 87: 2778-2786, 2004.

\* cited by examiner

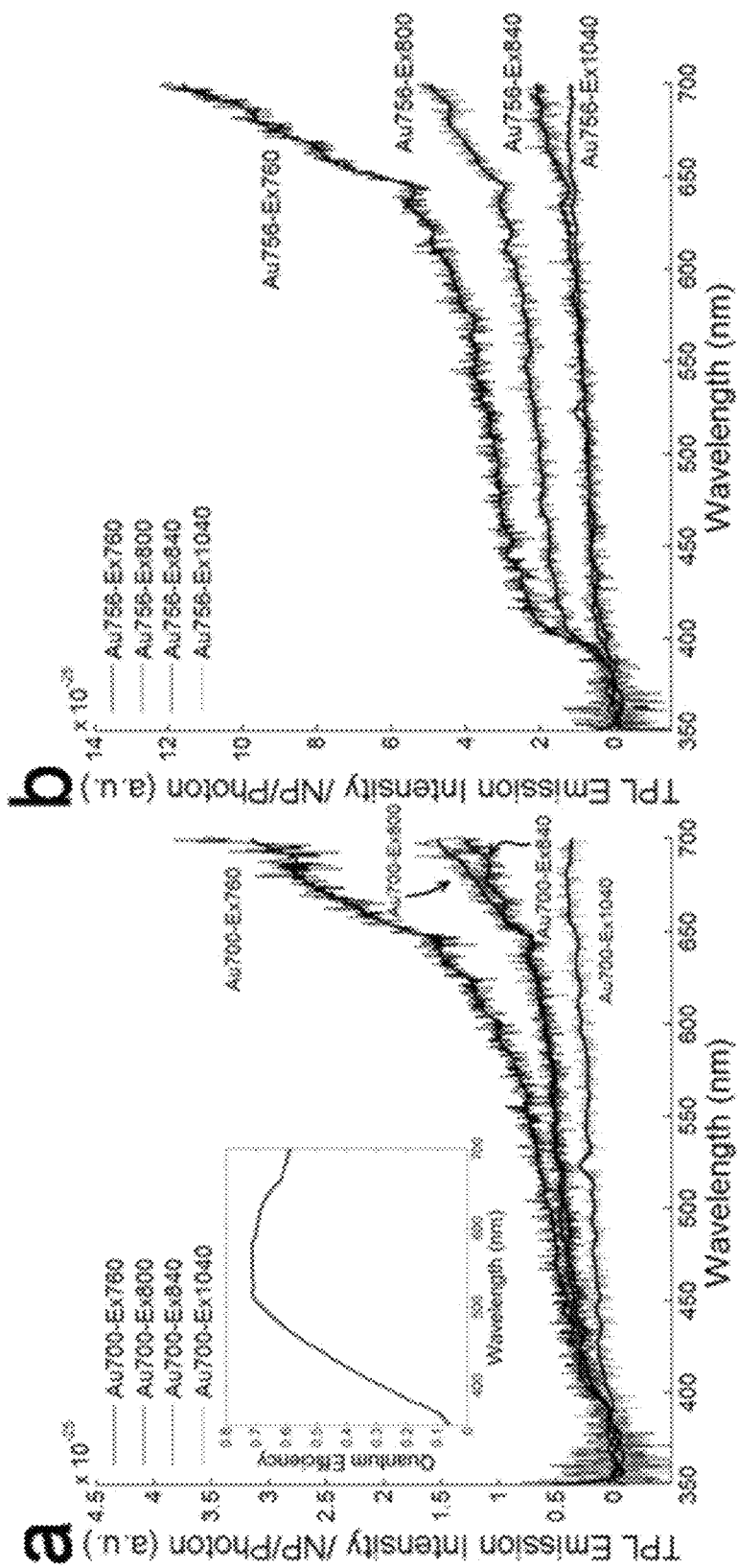
FIG. 14A-B

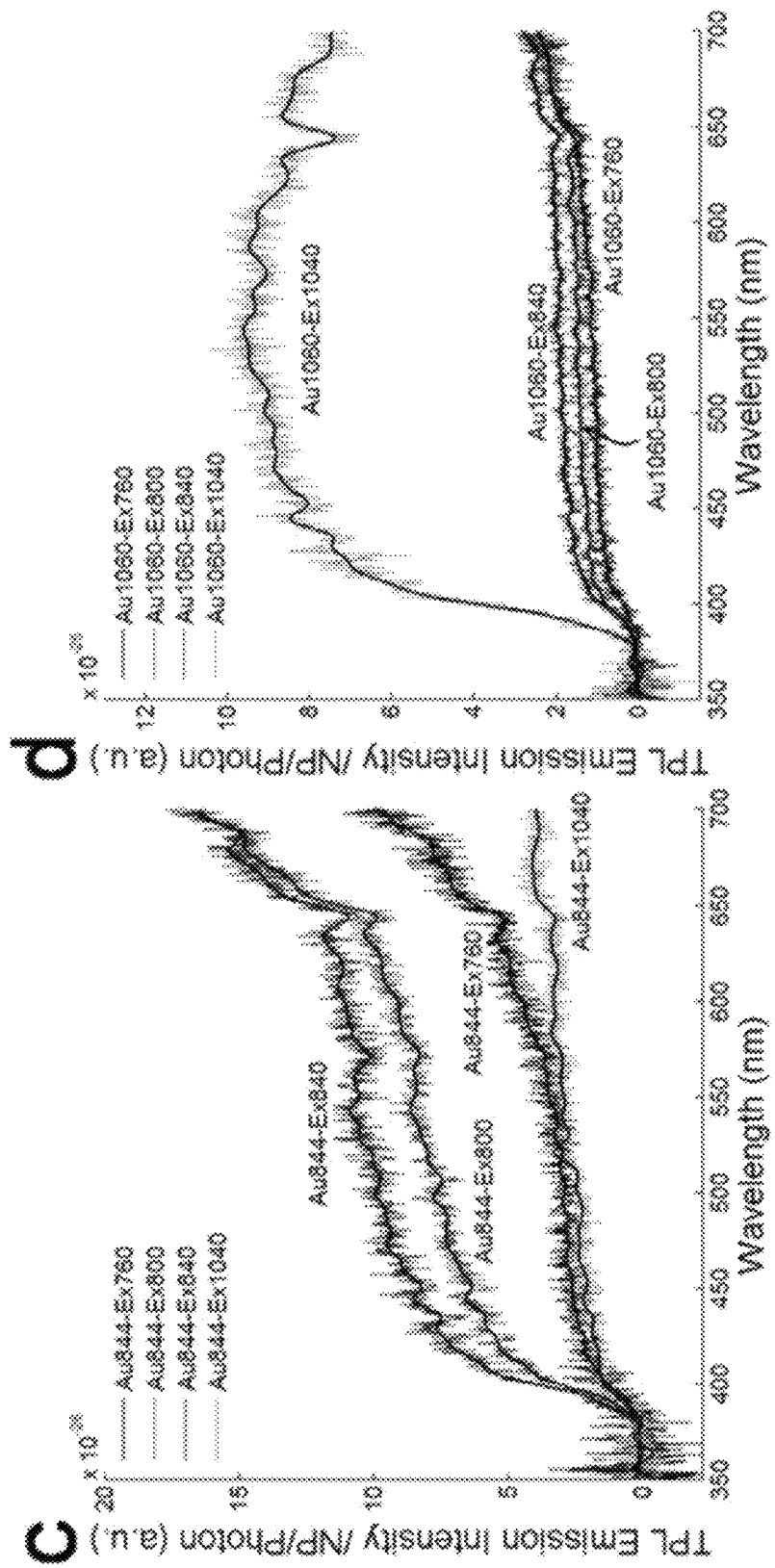
FIG. 14C-D

APPARATUS AND METHODS FOR OPTICAL COHERENCE TOMOGRAPHY AND TWO-PHOTON LUMINESCENCE IMAGING

CROSS-REFERENCE TO RELATED APPLICATIONS

This application claims priority to U.S. Provisional Patent Application Ser. No. 61/785,030, filed Mar. 14, 2013, the contents of which are incorporated by reference herein.

BACKGROUND INFORMATION

Atherosclerosis and plaque rupture leading to myocardial infarction remain the leading cause of death worldwide [1]. Inflammation and underlying cellular and molecular mechanisms [2-4] contribute to atherogenesis from initiation through progression, plaque rupture and ultimately, thrombosis. The vulnerable plaque, recently defined by Virmani [5] as "thin-cap fibroatheroma", results from inflammation and is characterized as having a thin fibrous cap typically less than 65 μm thick, increased infiltration of macrophages with decreased smooth muscle cells, and an increased lipid core size compared to stable plaques [6-8].

Several cellular and molecular events that lead to rupture of thin-cap fibroatheromas are now understood and being utilized to develop novel imaging approaches. Accumulations of macrophages in thin-cap fibroatheromas over-express matrix metalloproteinases (MMPs) [9-12] which are believed to contribute to vulnerability of thin-cap fibroatheromas and increased thrombogenicity [13-15]. Macrophages are an important early cellular marker that indicates the risk of plaque rupture in the coronary, cerebral, and peripheral circulations. Since plaque vulnerability is related to cellular composition as well as anatomical structure, developing a diagnostic method that can simultaneously reveal both composition and structure is desirable to identify vulnerable plaques and would allow in vivo monitoring of macrophage density in longitudinal studies in response to cardiovascular interventions.

Intravascular OCT (IVOCT) is a recently developed catheter-based method for high-resolution intravascular imaging. Of the cardiovascular imaging modalities, IVOCT is the only approach that provides sufficient spatial resolution to image thin-cap fibroatheromas.

However, risk of plaque rupture cannot be easily assessed by only IVOCT images. Two-photon luminescence (TPL) microscopy uses nonlinear optical properties of tissue and has been utilized to image plaque components such as endothelial cells, smooth muscle cells [16], elastin fibers [17,18], oxidized LDL [19] and lipid droplets [20] based on their endogenous autofluorescence. More recently, it has been reported that macrophages loaded with nanoparticles can be detected by TPL microscopy [21,22]. Fiber-based OCT [23,24] and TPL microscopy [25-28] has been reported respectively using photonic crystal fibers to transmit broadband light for achieving higher spatial resolution or to transmit ultrashort pulses for system size minimization. However, a combined fiber-based OCT-TPL system has not been previously realized.

SUMMARY

Exemplary embodiments of the present disclosure include a combined catheter-based optical coherence tomography-two-photon luminescence (OCT-TPL) imaging system to detect, and further characterize the distribution of cellular components (e.g., macrophage, collagen/elastin fiber, lipid droplet) in thin-cap fibroatheromas with high spatial resolution in vivo. Components of the catheter-based OCT-TPL system can include light sources for OCT (e.g., 1310 nm) and TPL (e.g., 800 nm), detectors for OCT (e.g., balanced detectors) and TPL (e.g., photon multiplier tubes), the transmission-grating compressor compensating the group delay dispersion of TPL excitation pulses, the fiber (e.g., photonic crystal fiber) delivering light from both OCT and TPL light sources and transmitting TPL emission signals, and the imaging catheter. Embodiments of the present disclosure describe methods and apparatus for imaging and related diagnostic and therapeutic catheter-based modalities that require the simultaneous delivery of short pulsed laser light and broadband OCT light.

Certain embodiments include an apparatus comprising: an optical coherence tomography light source configured to emit a first wavelength; a splitter configured to direct the first wavelength emitted from the coherence tomography light source to a reference path and to a sample path; a short-pulsed light source configured to emit a second wavelength; a first dichroic element; and a second dichroic element. In particular embodiments, the optical coherence tomography light source may be configured as a swept source optical coherence tomography light source. In certain embodiments, the optical coherence tomography light source may be configured as a broadband optical coherence tomography light source. In some embodiments, the short-pulsed light source may be a short-pulsed laser having a pulse energy between 10 pJ-1 mJ and a pulse duration between 5 fs-100 ps. In specific embodiments, the sample path may be directed through a photonic crystal fiber. Certain embodiments may include a balanced detector, and in particular embodiments, the balanced detector may be configured to minimize a non-interfering OCT component.

Particular embodiments may include a photon counting detector, and in certain embodiments, the photon counting detector may be a photomultiplier tube. In specific embodiments, the photon counting detector may be an avalanche photo diode. In some embodiments, the photon counting detector may be configured to detect two-photon luminescence. In certain embodiments, the second dichroic element may be configured to direct two photon luminescence toward a photon counting detector. In particular embodiments the first dichroic element may be configured to direct the first and second wavelengths to the sample path. In certain embodiments, the sample path may be directed to a sample site that comprises nanoparticles.

Particular embodiments may further comprise a visual display configured to display an image of the sample site. In certain embodiments, the visual display may be configured to enhance a portion of the display of the sample site based on the distance between the apparatus and the sample site. In some embodiments, the visual display may be configured to increase the brightness of a location of the sample site where a detected value exceeds a normalized value. In specific embodiments, the nanoparticles may be configured as nanorods. In certain embodiments, the nanorods comprise gold and have a surface plasmon resonance of approximately 756 nm. Particular embodiments may further comprise a dispersion compensating element, and in some embodiments, the dispersion compensating element is configured to compensate dispersion differences between the reference path and the sample path. In certain embodiments, the dispersion compensating element is configured to pre-compensate two-photon luminescence excitation light.

Particular embodiments may also include a method of imaging a sample site, where the method comprises: emitting a first wavelength from an optical coherence tomography light source toward a sample site; emitting a second wavelength from a short-pulsed light source toward the sample site; detecting an optical coherence tomography signal from the sample site, wherein the optical coherence tomography signal is generated from the first wavelength; and detecting a two-photon luminescence emission signal from the sample site, wherein the two-photon luminescence emission signal is induced by the second wavelength. In certain embodiments, the short-pulsed light source may be a short-pulsed laser having a pulse energy between 10 pJ-1 mJ and a pulse duration between 5 fs-100 ps.

In some embodiments, the optical coherence tomography signal and the two-photon luminescence signal may be detected from a plurality sample sites. In particular embodiments, the sample comprises a tissue, and in specific embodiments, the tissue may be epithelial tissue or arterial tissue. In certain embodiments, the arterial tissue may be located in a coronary artery. In specific embodiments, the tissue may be a vascular luminal surface. In particular embodiments, the tissue may be oral mucosa. In some embodiments, the optical coherence tomography signal may be used to generate an optical coherence tomography tomogram. In particular embodiments, the two-photon luminescence signal may be co-registered with an optical coherence tomography tomogram. Certain embodiments may further comprise displaying two-dimensional two-photon luminescence data on a three-dimensional optical coherence tomography tomogram. In some embodiments, a first processing element may use the optical coherence tomography signal and construct an optical coherence tomography tomogram.

In some embodiments, the first processing element may be a central processing unit or a graphics processing unit. In particular embodiments, a second processing element renders for viewing a co-registered two-photon luminescence image on an optical coherence tomography tomogram. In certain embodiments, the sample site may comprise a nanoparticle. In particular embodiments, the two-photon luminescence signal may be emitted from the nanoparticle. In specific embodiments, the two-photon luminescence emission signal may be emitted from tissue of the sample site.

Certain embodiments include a method for displaying imaging data, where the method comprises: obtaining optical coherence tomography data with an imaging system; obtaining two-photon luminescence data from a plurality of luminescing particles with the imaging system; and simultaneously displaying the optical coherence tomography data and the two-photon luminescence data in a combined image. In some embodiments, the luminescing particle may be a nanoparticle. In particular embodiments, the imaging system may be a catheter-based imaging system.

In certain embodiments, the optical coherence tomography data may comprise radial and azimuthal dimensional data, and the two-photon luminescence data may comprise an azimuthal signal. Particular embodiments may further comprise adding a radial dimension to the two-photon luminescence data. In certain embodiments, adding the radial dimension to the two-photon luminescence data may comprise using a radial probability distribution function that is normalized by the two-photon luminescence azimuthal signal. In specific embodiments, the radial probability distribution function may be determined using: optical properties of the imaging system; the distance between the catheter-based imaging system and a lumenal wall into which the catheter-based imaging system is inserted; and the optical properties of tissue of the lumenal wall.

In particular embodiments, the radial probability distribution function may be determined using assuming a uniform distribution of nanoparticles. Certain embodiments may further comprise generating three-dimensional images based on data obtained from the catheter-based imaging system as the catheter-based imaging system is moved axially along a lumen.

In the following, the term "coupled" is defined as connected, although not necessarily directly, and not necessarily mechanically.

The use of the word "a" or "an" when used in conjunction with the term "comprising" in the claims and/or the specification may mean "one," but it is also consistent with the meaning of "one or more" or "at least one." The term "about" means, in general, the stated value plus or minus 5%. The use of the term "or" in the claims is used to mean "and/or" unless explicitly indicated to refer to alternatives only or the alternative are mutually exclusive, although the disclosure supports a definition that refers to only alternatives and "and/or."

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a method or device that "comprises," "has," "includes" or "contains" one or more steps or elements, possesses those one or more steps or elements, but is not limited to possessing only those one or more elements. Likewise, a step of a method or an element of a device that "comprises," "has," "includes" or "contains" one or more features, possesses those one or more features, but is not limited to possessing only those one or more features. Furthermore, a device or structure that is configured in a certain way is configured in at least that way, but may also be configured in ways that are not listed.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will be apparent to those skilled in the art from this detailed description.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The following drawings form part of the present specification and are included to further demonstrate certain aspects of the present disclosure. The invention may be better understood by reference to one of these drawings in combination with the detailed description of specific embodiments presented herein.

FIG. 14 shows data obtained from an apparatus according to an exemplary embodiment.

DETAILED DESCRIPTION OF ILLUSTRATIVE EMBODIMENTS

Figure 1:
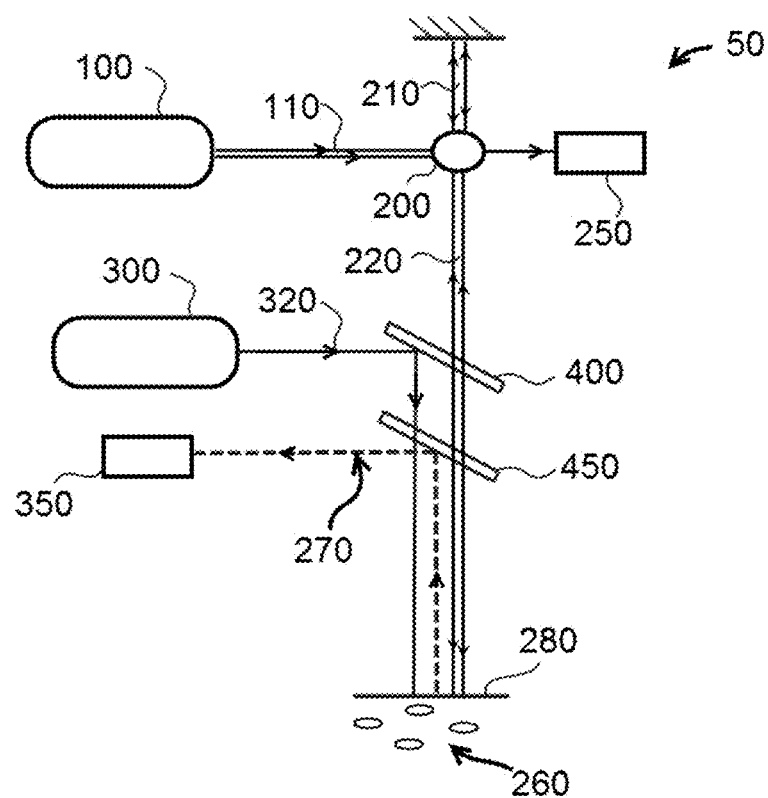
FIG. 1 shows a schematic of an apparatus according to an exemplary embodiment.

Referring now to FIG. 1, one exemplary embodiment of an apparatus 50 comprises an optical coherence tomography light source 100, a splitter 200, a two-photon luminescence excitation light source 300, a first dichroic element 400 and a second dichroic element 450. In this embodiment, optical coherence tomography light source 100 is configured to emit a first wavelength 110 and splitter 200 is configured to direct first wavelength 110 to a reference path 210 and a sample path 220. In certain embodiments, optical coherence tomography light source 100 can be configured as a swept source optical coherence tomography light source or a broadband optical coherence tomography light source. In particular embodiments, sample path 220 can be directed through a photonic crystal fiber. In the embodiment shown, two-photon luminescence excitation light source 300 is configured to emit a second wavelength 320.

During operation, apparatus 50 can be positioned such that sample path 220 and second wavelength 320 are directed to a sample site 280 (e.g. via first dichroic element 400 as well as other components in FIG. 1).

In certain exemplary embodiments, sample site 280 may comprise nanoparticles 260 and in specific embodiments, nanoparticles 260 may be configured as nanorods. In particular embodiments, nanoparticles 260 may be configured as nanorods comprising gold with a surface plasmon resonance of approximately 756 nm. In certain embodiments, the configuration of the nanorods can be selected according to the procedures established in the Example Section 4 provided below.

Apparatus 50 further comprises a photon counting detector 350 configured to detect two-photon luminescence (TPL) and a balanced detector 250 configured to minimize a non-interfering OCT component. In specific embodiments, photon counting detector 350 can be configured as one or more photomultiplier tubes (PMTs). In other embodiments, photon counting detector 350 can be configured as an avalanche photo diode.

In a particular embodiments, components of the system illustrated in FIG. 1 can be incorporated into a catheter-based system that utilizes a photonic crystal fiber (PCF) to enable the propagation of light in sample path 220 and second wavelength 320 from TPL excitation light source 300 to sample site 280. The PCF allows single-mode transmission of both OCT and TPL excitation light. Single-mode transmission is required in OCT imaging to insure the modal interference does not occur. Single mode transmission is required for TPL imaging to insure the pulse duration of TPL excitation light is not broadened due to modal dispersion. In specific embodiments the catheter can be inserted into a blood vessel to obtain intravascular images utilizing system 50.

During operation, system 50 provides the benefits of both OCT and TPL imaging technologies in a single system. In exemplary embodiments, the components of system 50 function according to established principles in OCT and TPL fields. Accordingly, while an overview of the individual OCT and TPL will be provided, it is understood that exemplary embodiments may utilize various combinations of parameters according to environmental conditions or other factors. For example, OCT light source 100 can produce near-infrared light, and the use of relatively long wavelength light allows deeper penetration into the scattering medium such as an arterial wall. In a particular embodiment OCT light source 100 can be configured to provide light at a wavelength of approximately 1310 nm.

As light in sample path 220 is directed at sample site 280, a small portion of this light that reflects from sub-surface features of sample site 280 is collected. During operation, a significant portion of light in sample path 220 is not reflected but, rather, backscatters from the sample. Although backscattered light contributes background that obscures an image in conventional imaging, this light can be used beneficially in OCT systems via interferometry. For example, balanced detector 250 can be used to record the optical path length of received photons, allowing rejection of most photons that multiply scatter in the tissue before detection. This can allow recording three-dimensional images of thick samples to be constructed by rejecting background signal while collecting light directly reflected from regions of interest in sample site 280. In exemplary embodiments, OCT imaging is generally limited to one to two millimeters below the surface in biological tissue in sample site 280. At greater depths, the proportion of light that escapes without scattering is typically too small for detection.

During operation of system 50, TPL light source 300 and photon counting detector 350 are also utilized consistent with established principles in two-photon luminescence microscopy. In certain embodiments, TPL light source 300 can be configured as a tunable femtosecond laser producing excitation energy of second wavelength 320 at 760-1040 nm with a maximum pulse energy of 6 nJ-5 µJ, a pulse width of 100 fs-1 ps, and a repetition rate of 500 kHz-80 MHz. In particular embodiments, TPL light source 300 may also be configured to produce a spot size of 10-30 µm with a spot area of approximately 78-706.8 µm$^2$ and a pixel dwell time of 20 µs. In addition, TPL light source 300 may also be configured to produce 10-1600 pulses per pixel, with an average power on sample of 500-2500 mW, an instantaneous power of 0.0625-5 MW and an instantaneous power density of 2E-4-16E-3 MW/µm$^2$.

In the embodiment shown in FIG. 1, first dichroic element 400 can be positioned to direct second wavelength 320 to sample site 280 via a photonic crystal fiber (PCF). In particular embodiments, the PCF can have a large sized mode field diameter (20 μm) (LMA-20) available from NKT Photonics. In certain embodiments, the PCF may be configured as a double-clad fiber, and in specific embodiments, may be a double-clad high NA fiber such as a model number DC-165-16-Passive Fiber available from Crystal Fibre. Exemplary double-clad photonic crystal fibers may comprise a large-mode area, single-mode core embedded in a high-NA multimode fiber structure. Such fibers can allow a single-mode beam to be propagated forward in the fiber and at the same time scattered light or two-photon luminescence may be collected and propagated backwards for detection. The use of a double-clad fiber instead of a single-clad photonic crystal fiber can increase the two-photon luminescence detection efficiency with a high-NA inner cladding (compared to the low-NA core). It is understood that the particular specifications of components are presented for purposes of example only, and that other embodiments may comprise components with different specifications than those described herein.

During operation of system 50, second wavelength 320 can provide excitation energy to nanoparticles 260, which can emit luminescence 270 that is directed to photon counting detector 350 via second dichroic element 450. In exemplary embodiments, the outputs from the photon counting detector 350 and balanced detector 250 can be configured to be combined in a single display that allows a user to visualize the results of both OCT and TPL imaging overlayed.

The display of the intravascular OCT and TPL images presents certain challenges to presenting the information to a user in a manner that can be quickly interpreted in a way that provides useful data. For example, intravascular OCT is two-dimensional (radial and azimuthal) while the TPL information in some embodiments is one-dimensional (azimuthal). A one-dimensional display of the TPL azimuthal information as a ring or band either inside or outside of the two-dimensional IV-OCT image was also evaluated as a way to present the combined IV-OCT and TPL image information.

Exemplary embodiments for displaying the combined IV-OCT and TPL comprise incorporating a radial dimension to the TPL data that uses a radial probability distribution function [p(r)] that will be normalized by the TPL azimuthal signal at that position. The radial probability distribution function [p(r)] can be determined from (in part): (1) the optics of the catheter; (2) distance between the catheter and lumenal wall; (3) tissue optical properties. This information can be combined to predict the radial dependence [p(r)] of the TPL signal that assumes a uniform distribution of nanoparticles 260.

With TPL information that includes both azimuthal and radial dependencies, the TPL and IV-OCT images can be fused to show both sets of information in one image data set. In addition, the same procedure can be followed for the entire pullback so that the three-dimensional IV-OCT and TPL datasets can be fused into a single image dataset.

Figure 2:
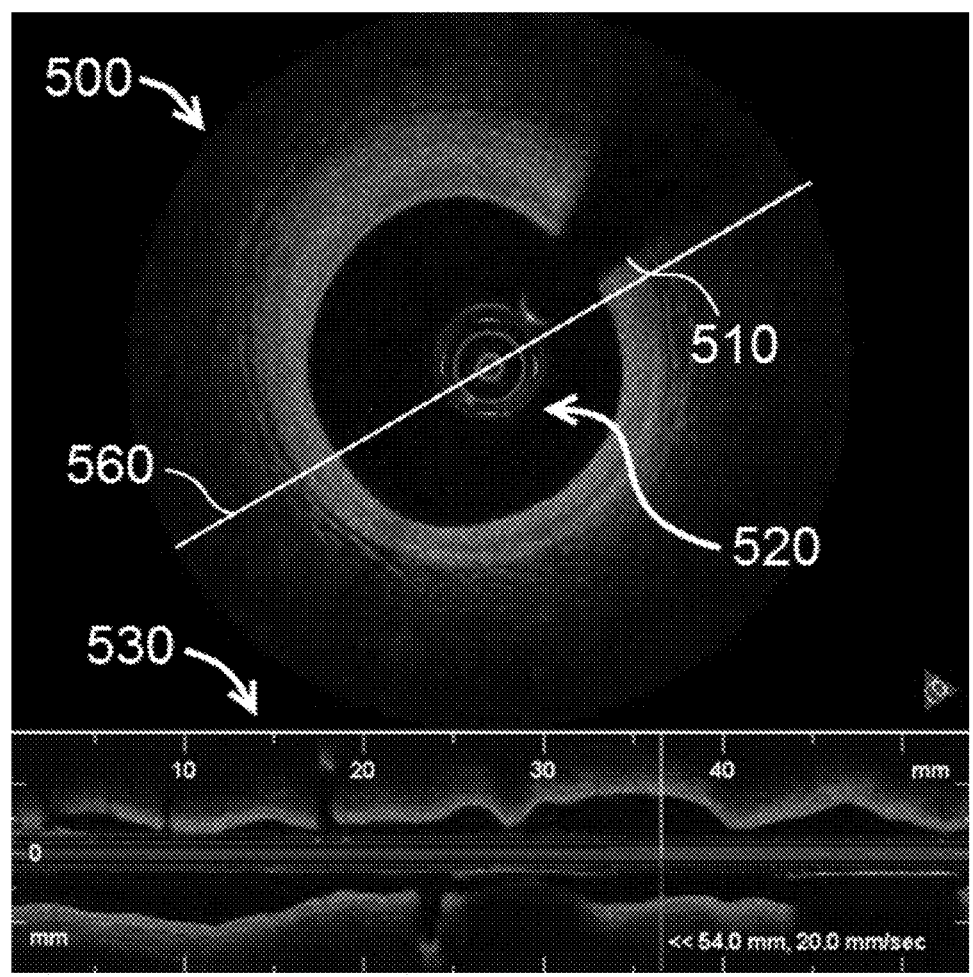
FIG. 2 shows an image obtained from an IV-OCT system.

Referring now to FIG. 2, an IV-OCT image 500 is produced using a catheter 510 configured to produce a typical IV-OCT image without combined TPL data. As shown in FIG. 2, image 500 shows a healthy coronary artery 520 with a substantially uniform wall. A side section view 530 of artery 520 is shown in the lower portion of FIG. 2. Side section view 530 is a reconstructed view of artery 520 taken along line 560 during pullback of catheter 510.

Figure 3:
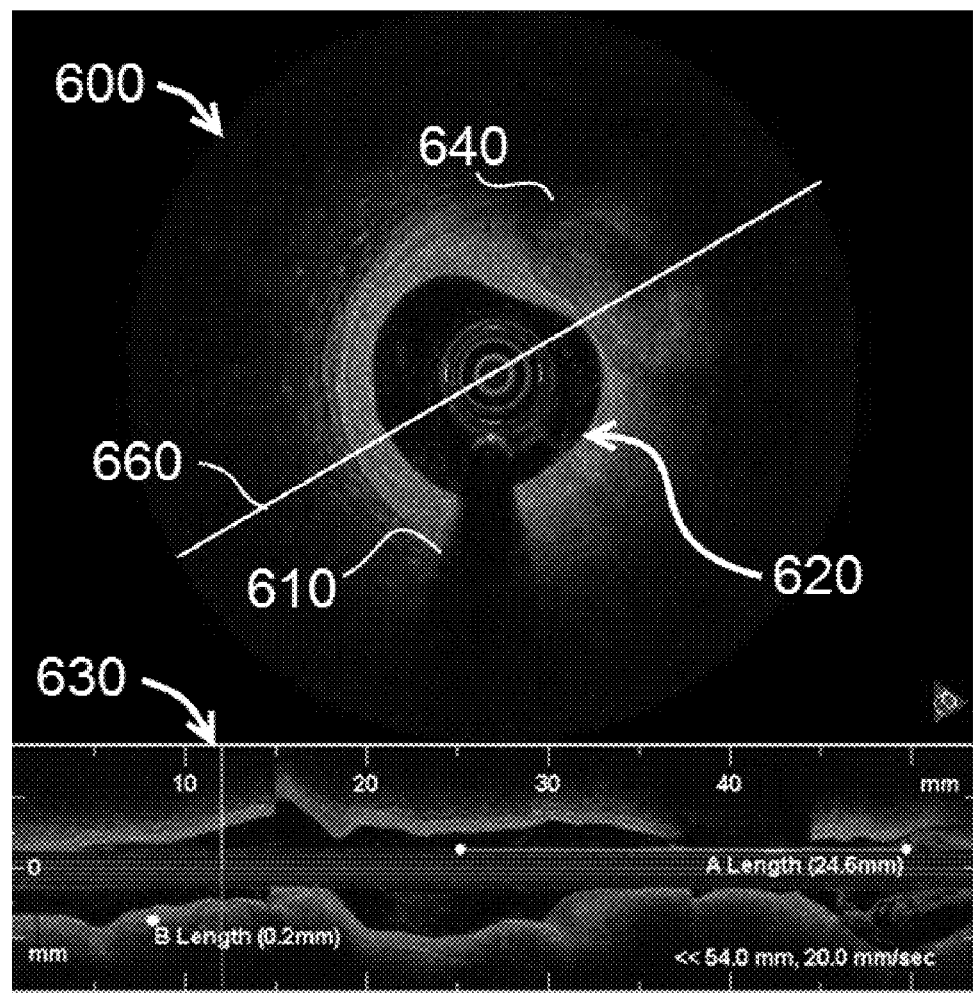
FIG. 3 shows an image obtained from an IV-OCT system.

Referring now to FIG. 3, an IV-OCT image 600 is produced using a catheter 610 configured to produce a typical IV-OCT image, also without combined TPL data. As shown in FIG. 3, image 600 shows a coronary artery 620 with a thin-cap fibroatheroma 640 overlying a large lipid core at approximately the 1:00-3:00 position. A side section view 630 of artery 620 is shown in the lower portion of FIG. 3. Side section view 630 is a reconstructed view of artery 620 taken along line 660 during pullback of catheter 610.

While image 600 shows thin-cap fibroatheroma 640, the risk of plaque rupture cannot be easily assessed from the image provided. Image 600 provides a view of the anatomical structure, but does not allow a user to evaluate the cellular composition. For example, image 600 does not directly provide an indication of the presence of macrophages, lipid deposits and collagen/elastin fibers, early cellular markers that can indicate the risk of plaque rupture.

Figure 4:
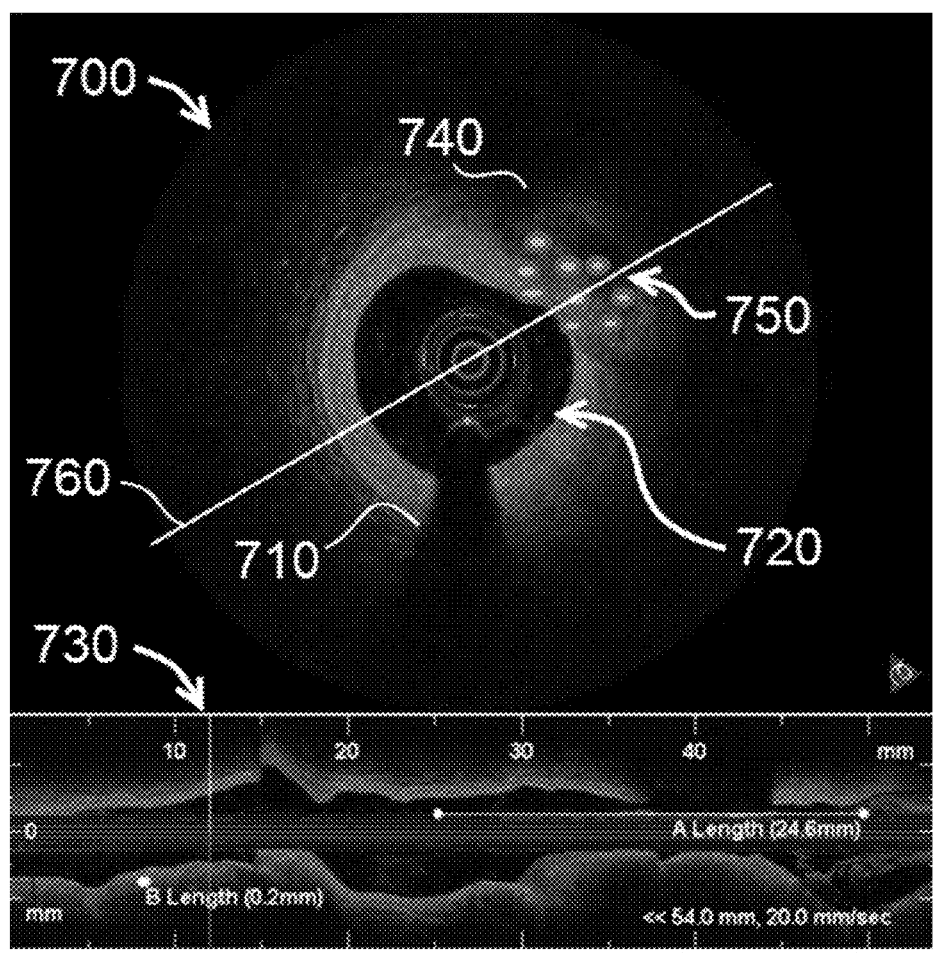
FIG. 4 shows an image obtained from an apparatus according to an exemplary embodiment.

Embodiments of the present invention (including, for example, system 50 shown in FIG. 1 or the specific example systems shown in FIG. 5A, 5B, 6 or 7) are configured to provide a combined OCT-TPL image, similar to that of image 700 as illustrated in FIG. 4. Image 700 can be produced by a combined OCT-TPL system examining a section of coronary artery. For example, coronary artery 720 comprises a thin-cap fibroatheroma 640 overlying a large lipid core at approximately the 1:00-3:00 o'clock position.

Unlike the image in FIG. 3, the image shown in FIG. 4 (an enhanced OCT-TPL image) does provide a user both a view of the anatomical structure and the ability to analyze the cellular composition of the structure. For example, a photon counting detector in exemplary OCT-TPL systems can detect two-photon luminescence (TPL) 750 from nanoparticles that may be concentrated in the thin-cap fibroatheroma 740 cellular components, including for example, macrophages, elastin fibers, and/or lipid droplets. The combined image of the anatomical structure, as well as indication of the cellular composition of the structure, can allow a user to perform a more thorough analysis of the plaque rupture risks associated with specific structures.

Exemplary embodiments of the present disclosure may also comprise computer readable media (e.g. Software) to quantitatively analyze images obtained by the apparatus and enhance the visual display of certain aspects. For example, if a catheter is not centered within a vascular lumen, light that is emitted from a site of interest that is farther away from the catheter may not appear as bright to the naked eye (as compared to light emitted from a site that is closer to the catheter).

Figure 15:
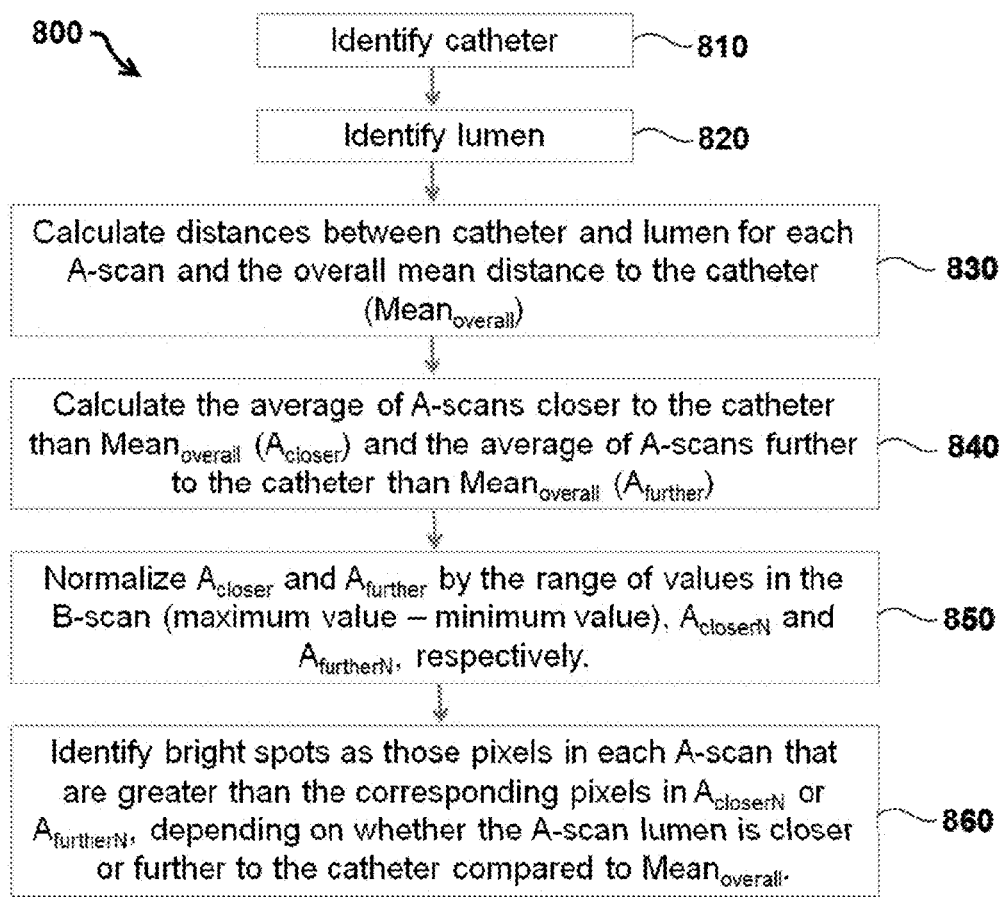
FIG. 15 shows a flowchart of steps performed by a computer readable medium to modify the display of data results according to an exemplary embodiment.
Figure 16:
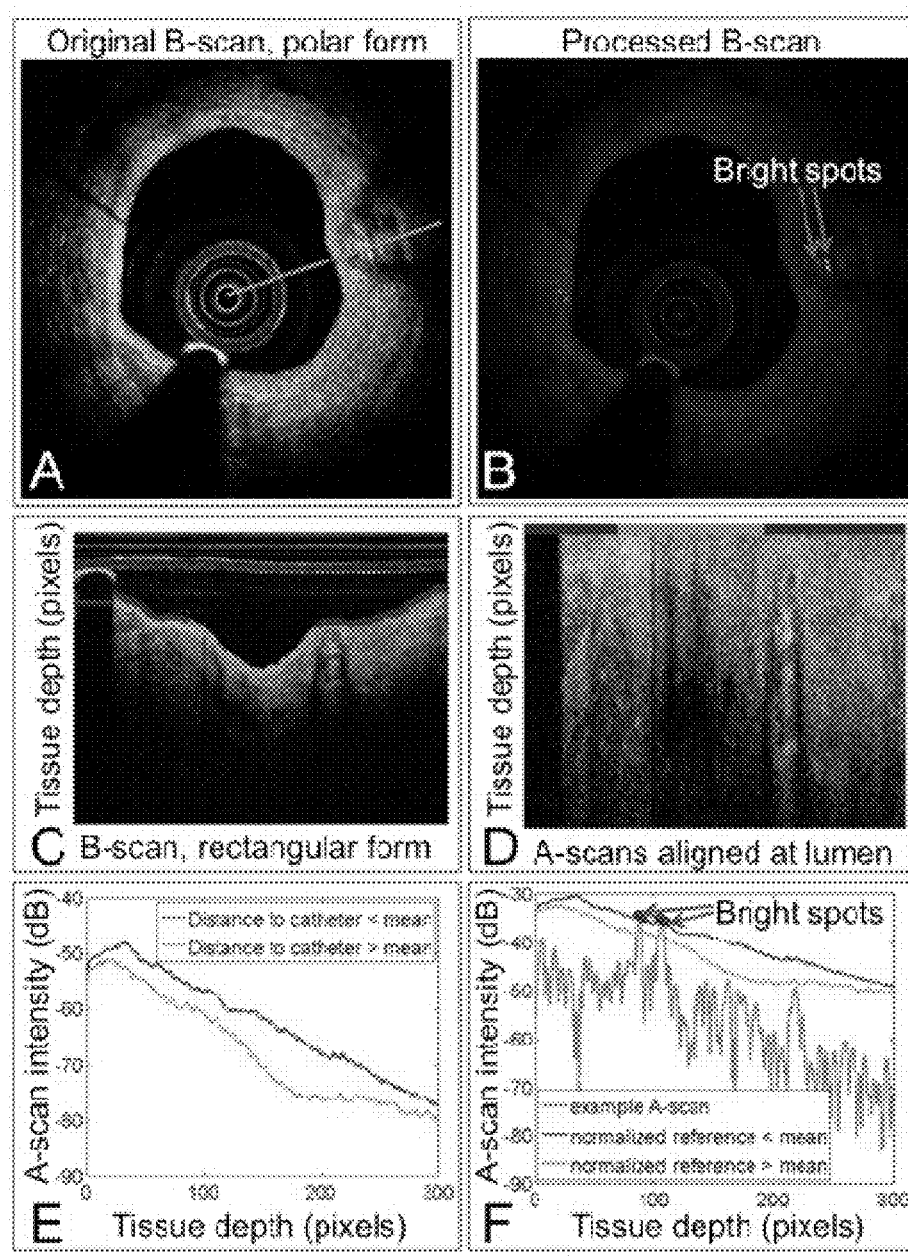
FIG. 16 shows an image and data obtained from an apparatus according to an exemplary embodiment.

Referring now to FIGS. 15-16, in one embodiment a computer readable medium can be configured to perform the following steps of a process 800: (1) identify the catheter in step 810; (2) identify the lumen (e.g. the vascular wall of the tissue being analyzed) in step 820; (3) calculate distances between the catheter and the lumen for each A-scan and the overall mean distance to the catheter (Meanoverall) in step 830; (4) calculate the average of A-scans closer to the catheter than Meanoverall (Acloser) and the average of A-scans further to the catheter than Meanoverall (Afurther) in step 840; (5) normalize Acloser and Afurther by the range of values in the B-scan (maximum value-minimum value), AcloserN and AfurtherN, respectively in step 850; and (6) identify bright spots as those pixels in each A-scan that are greater than the corresponding pixels in AcloserN or AfurtherN, depending on whether the A-scan lumen is closer or further to the catheter compared to Meanoverall in step 860.

Additionally, performing the averaging of A-scans to identify bright spots can be replaced by scaling each A-scan by the Gaussian shape of the catheter beam to correct for intensity vs. depth.

Referring specifically now to FIG. 16A, an unprocessed image is shown in comparison to a processed image in FIG. 16B. In FIG. 16C, a B-scan image is shown in rectangular form. It can be noted that the portion of the B-scan highlighted with a blue indication line are taken from locations with a distance between the catheter and lumen wall that is less than the mean distance. Likewise, the portion of the B-scan highlighted with a green indication line is taken from locations with a distance between the catheter and lumen wall that is less greater than the mean distance. FIG. 16D shows the A-scans aligned at the lumen. FIG. 16F shows an example A-scan (in magenta) as well as normalized reference values for those locations where the distance between the catheter and lumen wall that is less than the mean distance (in blue) and greater than the mean distance (in green).

The locations where the example scan in FIG. 16F exceed the normalized values can be identified as "bright spots" and the image enhanced as shown in FIG. 16B. This can allow a user to more objectively identify sites of interest that can be further investigated.

Exemplary embodiments are also capable of performing texture analysis by overlaying the OCT information with the TPL data. The dataset can be analyzed during three-dimensional rendering or processing to provide additional information to the doctor such as plaque locations, tissue type, and other physiological information. This information may be computed from the three-dimensional dataset using texture analysis, ray tracing, or other advanced processing techniques.

Exemplary embodiments of angle-resolved OCT systems may produce multiple three-dimensional datasets, in which case analysis would be done on all datasets and may or may not be combined to provide additional information to the doctor.

In summary, the combined OCT-TPL imaging system described herein can provide two optical contrast mechanisms: backscattering strength and two-photon luminescence. Embodiments of the catheter-based apparatus described herein may be utilized for light-based modalities that require the simultaneous single-mode delivery of both high peak power short-pulsed laser light and broadband light such as that utilized for OCT. Exemplary embodiments of the present disclosure combine IVOCT with TPL imaging in a catheter-based OCT-TPL imaging system to simultaneously image thin-cap fibroatheromas and its cellular components (e.g., macrophage, collagen/elastin fiber, lipid droplet) in vivo, which will have decided advantages over IVOCT alone and will provide cardiologists important information about the vulnerability of thin-cap fibroatheromas overtime during cardiovascular interventions. Specific configurations, features and methods of particular embodiments are set forth in the examples provided below.

EXAMPLE 1

Catheter-Based Intensity OCT-TPL System

Examples of the catheter-based intensity OCT-TPL system (shown in FIGS. 5A and 5B) can incorporate a spectral-domain OCT system operating at 1310 nm combined with TPL using a tunable femtosecond laser excitation (e.g., 760-1040 nm, 6 nJ-5 µJ, 100 fs-1 ps, 500 kHz-80 MHz). A pulse compressor can be utilized to pre-compensate the group dispersion delay of femtosecond laser light to provide transform-limited pulses on the luminal surface. The imaging catheter is connected to a photonic crystal fiber (PCF) (e.g., LMA-20, NKT Photonics) of the OCT-TPL imaging system, which can enable single-mode propagation of both OCT light and TPL excitation light and transmission of TPL emission light (e.g. the OCT light and TPL excitation light are transmitted simultaneously). In certain embodiments, the PCF may comprise a 15 µm core (e.g., LMA-15).

Figure 5A:
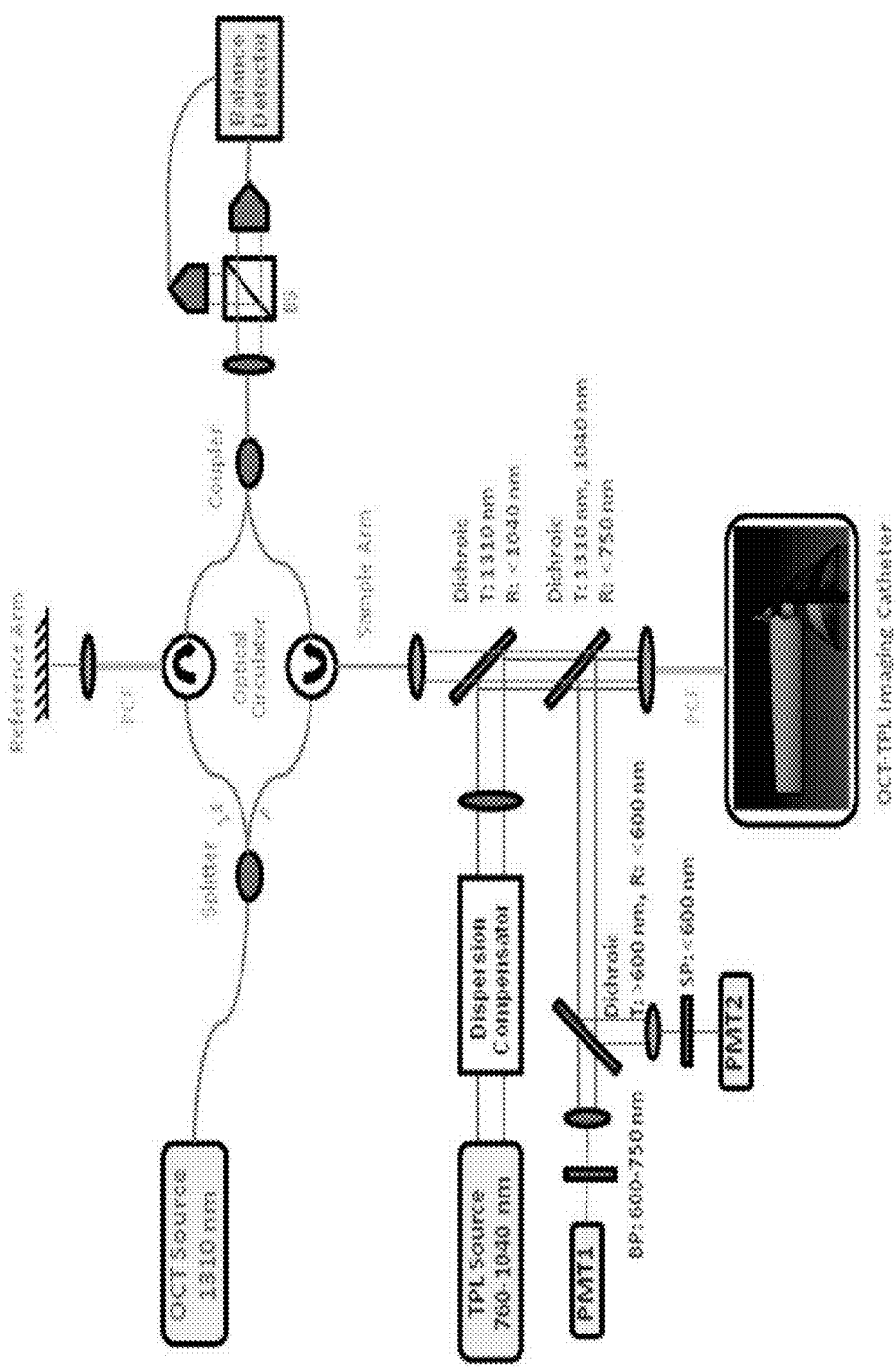
FIGS. 5A and 5B show a schematic of an apparatus according to an exemplary embodiment.

FIG. 5A depicts a catheter-based intensity OCT-TPL imaging system comprising a beam splitter (BS); band-pass filter (BP); short-pass filter (SP); photon multiplier tube (PMT); and a photonic crystal fiber (PCF). FIG. 5A illustrates an example in which the TPL excitation light is not transmitted through the dichroic mirrors to the PCF fiber.

Figure 5B:
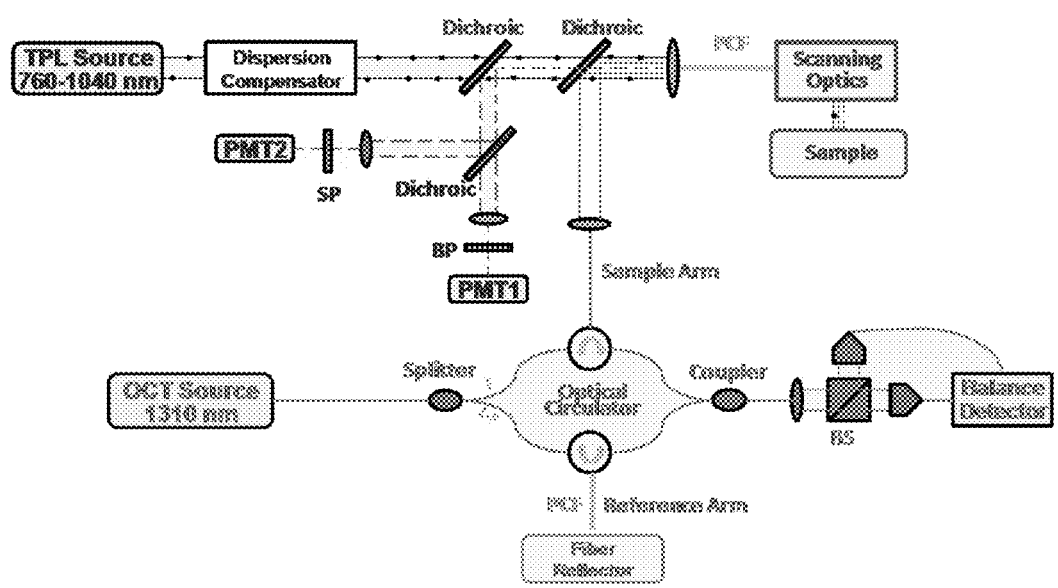
Figure 6:
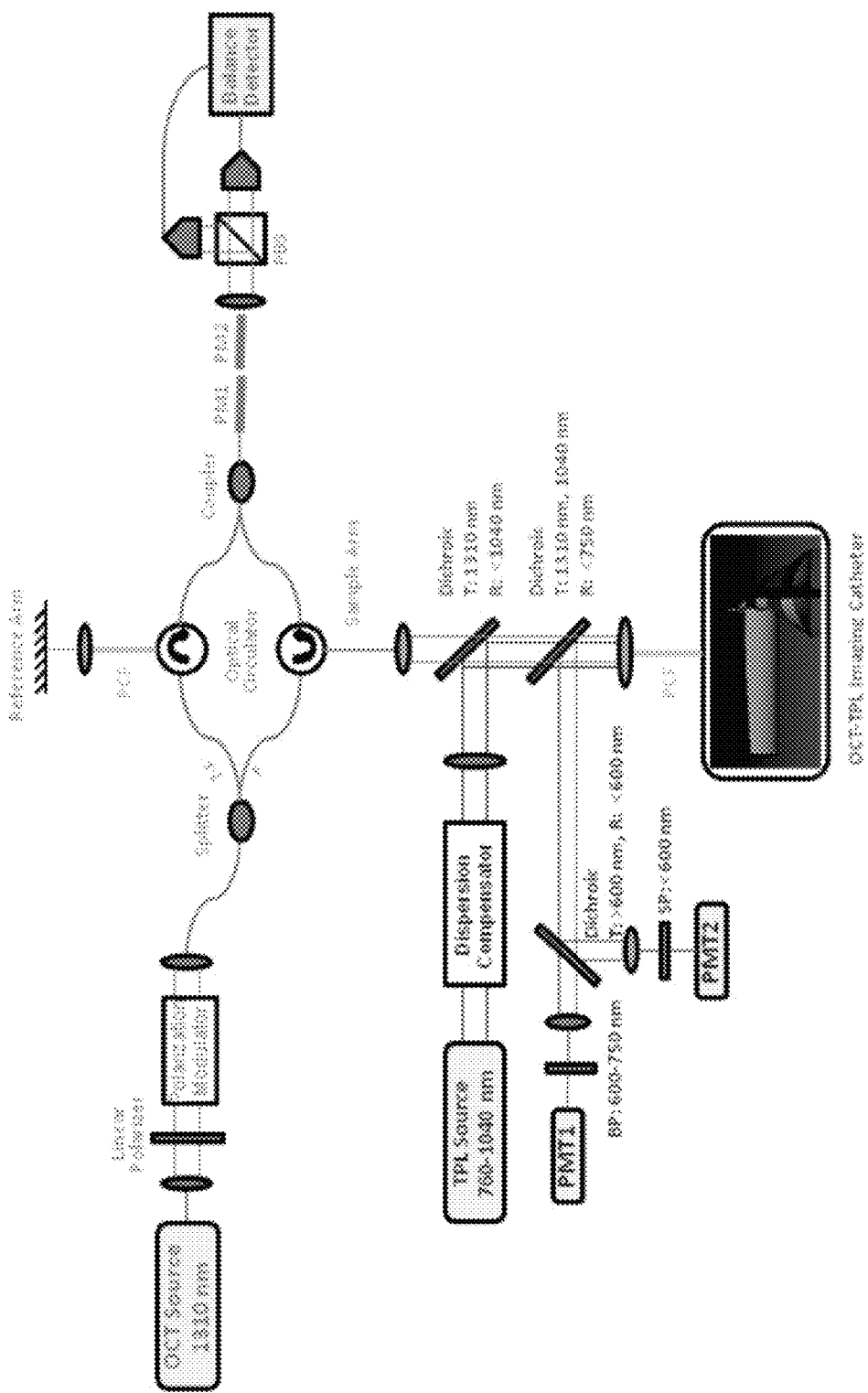
FIG. 6 shows a schematic of an apparatus according to an exemplary embodiment.
Figure 7:
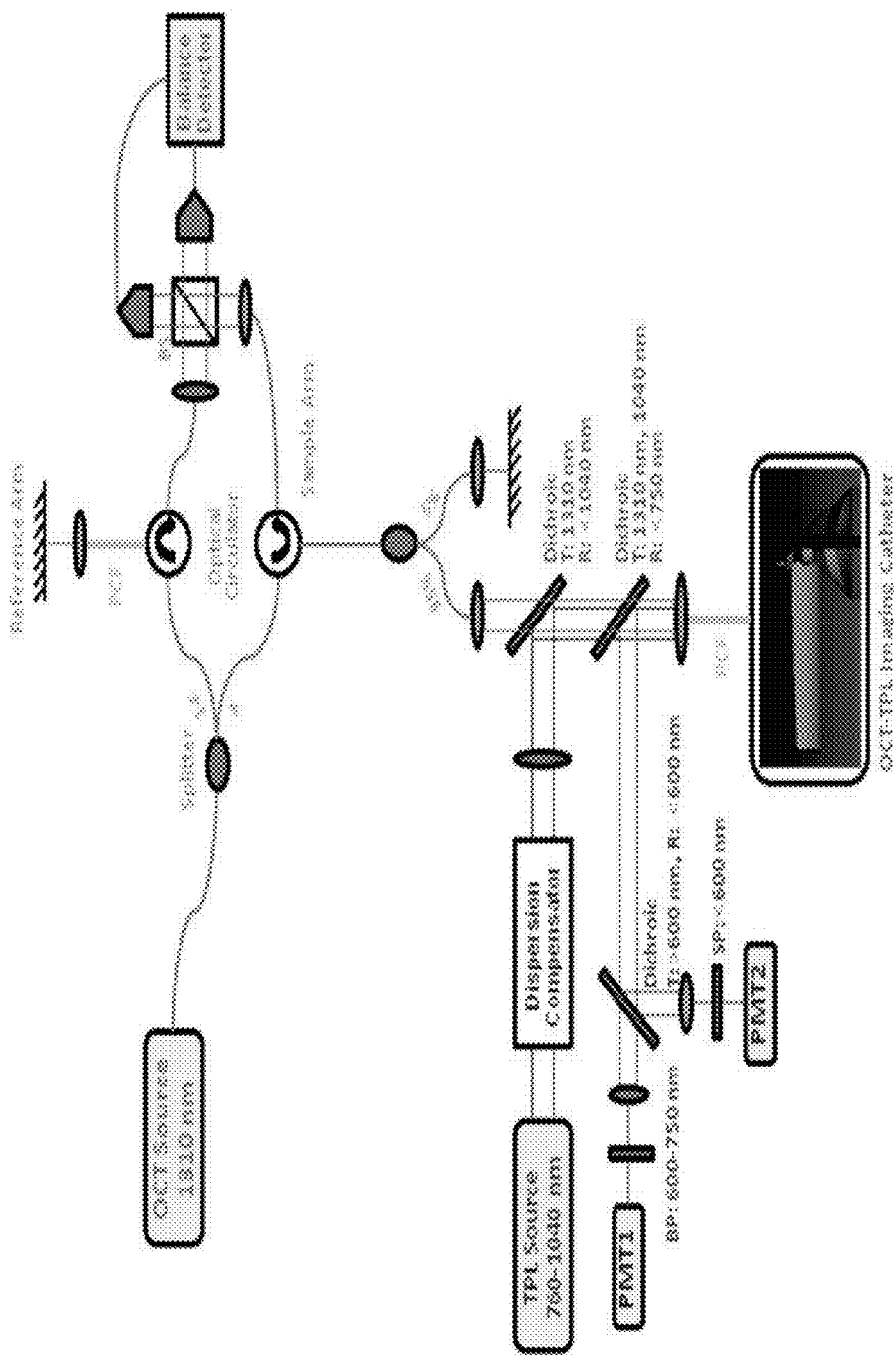
FIG. 7 shows a schematic of an apparatus according to an exemplary embodiment.

FIG. 5B also depicts a catheter-based intensity OCT-TPL imaging system comprising a beam splitter (BS); band-pass filter (BP); short-pass filter (SP); photon multiplier tube (PMT); and a photonic crystal fiber (PCF). In contrast, however, FIG. 5B illustrates an example in which a portion of the TPL excitation light is transmitted through the dichroic mirrors to the PCF fiber (and subsequently to a scanning optics module and the sample). As a result, the arrangement of the TPL and OCT light sources, as well as the associated instrumentation, is also different as shown in FIGS. 5A and 5B. In either configuration, a dispersion compensator could also be placed in OCT reference arm branch as known in the art.

Figure 17:
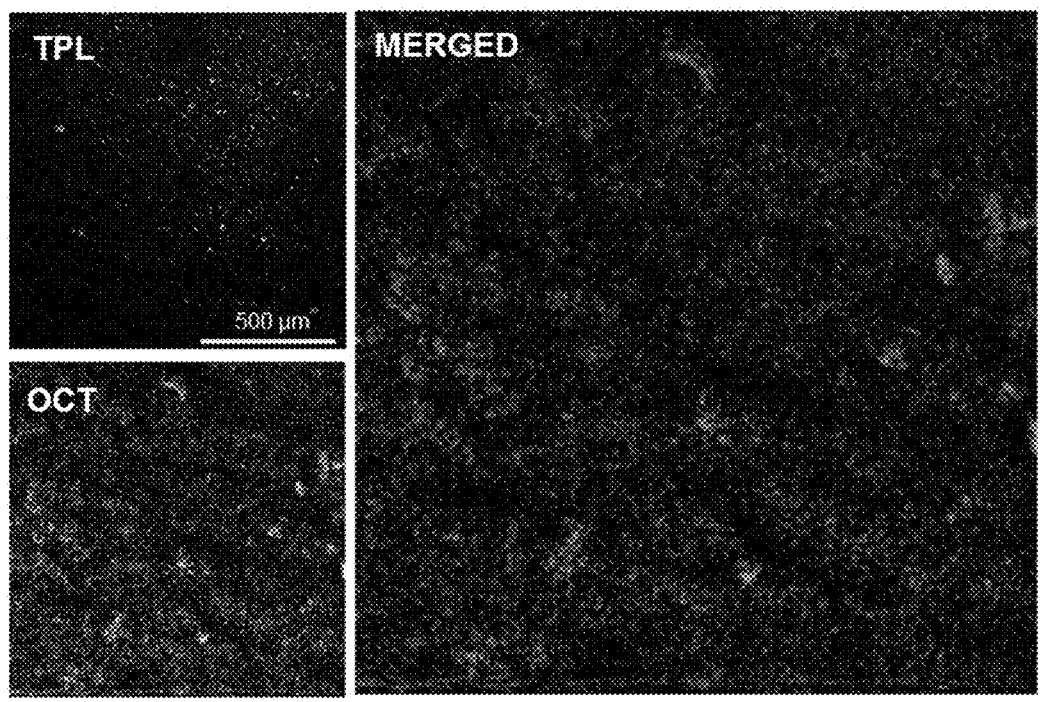
FIGS. 17-20 images obtained from an apparatus according to an exemplary embodiment.
Figure 18:
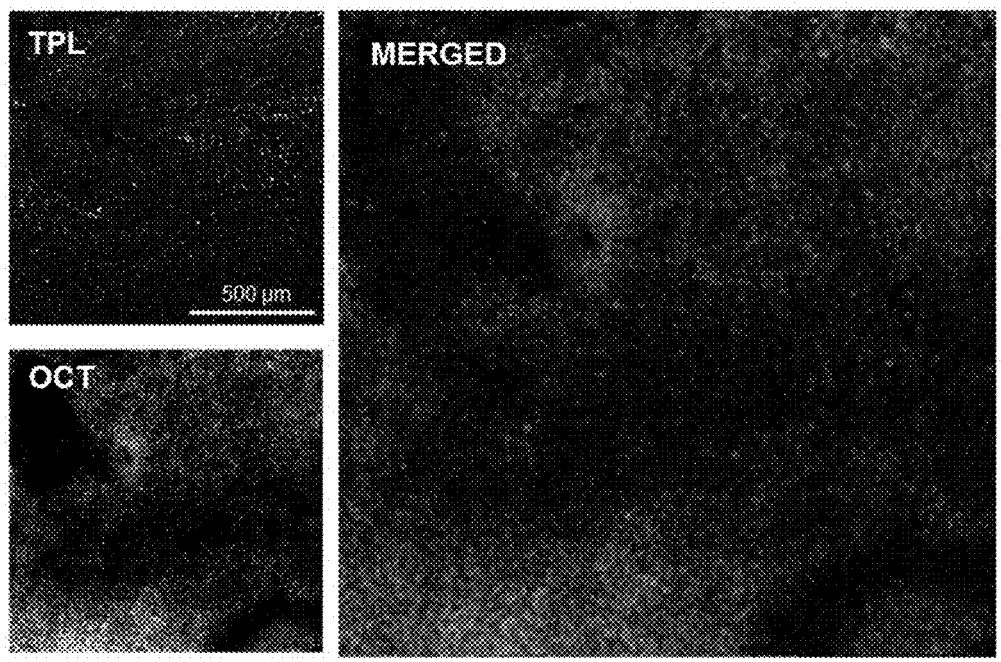

In certain embodiments, the systems shown in FIGS. 5A and 5B can be used to produce a merged image of TPL and OCT images. Examples of TPL, OCT and merged tissue images of a human coronary artery are shown in FIGS. 17 and 18. As shown in the figures, the merged image may use different colors to indicate the portion of the image obtained with OCT (in this example, green) and TPL (in this example, red).

During operation of the system used to produce the images in FIGS. 17 and 18, the OCT parameters were as follows—swept laser: 1310 nm/110 nm; beam size: 20 µm; laser power: 1.2 mW; field of view: 2 mm×2 mm; and A-scan rate: 20 kHz. In addition, the TPL parameters of the system used to produce the images of FIGS. 17 and 18 are as follows—2-P excitation laser: 760-1040 nm, 120 fs, 80 MHz; pixel dwell time: 4 µs; laser power: 500 mW; beam size: 20 µm; emission filter: <700 nm; field of view: 2 mm×2 mm.

Figure 19:
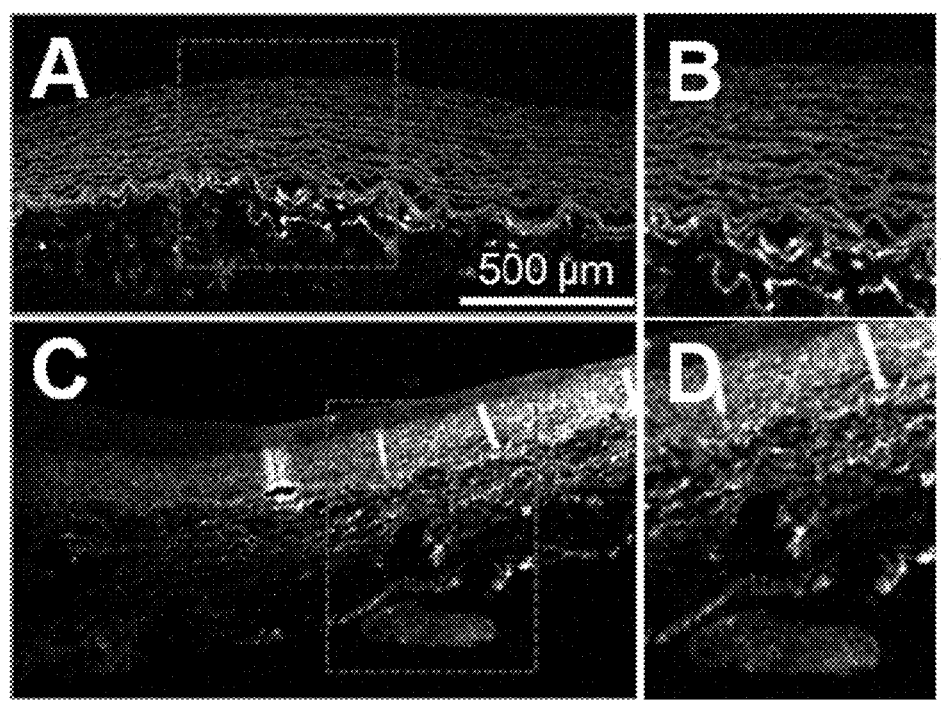

Referring now to FIG. 19, images are displayed that were obtained with TPL imaging techniques according to exemplary embodiments. The images display rabbit aorta tissue slices with atherosclerotic plaques. The bright TPL signals are native autofluorescence from lipid droplets, collagen and elastin fibers.

Figure 20:
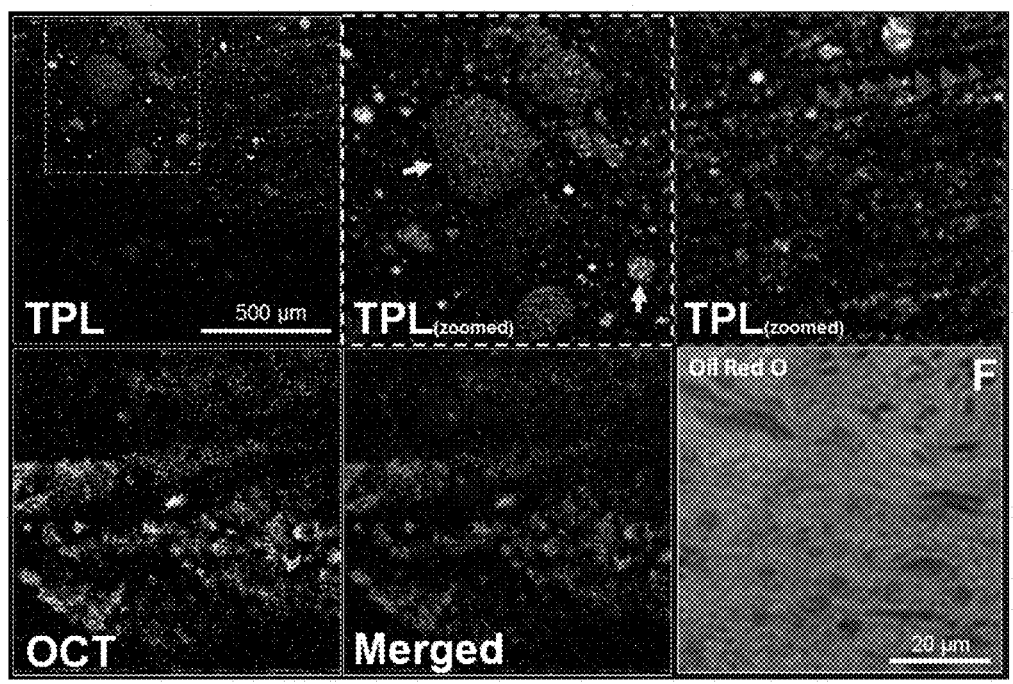

FIG. 20 displays TPL, OCT and merged TCL-OCT images of human coronary artery tissue obtained with a fiber-based system according to exemplary embodiments. In addition, the lower right portion of FIG. 20 comprises a stained tissue slice that indicates the distribution of lipids.

EXAMPLE 2

Catheter-Based Polarization-Sensitive OCT-TPL System

One example of the catheter-based polarization-sensitive OCT-TPL system (shown in FIG. 6) can incorporate a spectral-domain polarization-sensitive OCT (PSOCT) system operating at 1310 nm combined with TPL using a tunable femtosecond laser excitation (e.g., 760-1040 nm, 6 nJ-5 µJ, 100 fs-1 ps, 500 kHz-80 MHz). The system in FIG. 6 comprises polarization maintaining fiber segments (PM1 and PM2) that act as an in-line fiber polarimeter; a polarization beam splitter (PBS); a band-pass filter (BP); a short-pass filter (SP); a photon multiplier tube (PMT); and a photonic crystal fiber (PCF).

The PSOCT system utilizes balanced detection and an in-line fiber polarimeter [29] to measure the polarization state of both reference light and interference fringes. An open optical switch in the sample path of the interferometer allows measurement of a signal containing only the polarization state of reference light (without interference fringes between reference and sample light). A pulse compressor can be utilized to pre-compensate the group delay dispersion of femtosecond laser light to provide transform-limited pulses on the luminal surface. The imaging catheter can be connected to a photonic crystal fiber (PCF) (e.g., LMA-20, NKT Photonics) of the OCT-TPL imaging system, which can enable propagation of both OCT light and TPL excitation/emission light.

EXAMPLE 3

Catheter-Based Spectral Domain Phase-Sensitive OCT-TPL System

One example of a catheter-based phase-sensitive OCT-TPL system (shown in FIG. 7) can incorporate a spectral-domain phase-sensitive OCT (PhSOCT) system operating at 1310 nm combined with TPL using a tunable femtosecond laser excitation (e.g., 760-1040 nm, 6 nJ-5 µJ, 100 fs-1 ps, 500 kHz-80 MHz). The system of FIG. 7 comprises a polarization beam splitter (BS); a band-pass filter (BP); a short-pass filter (SP); a photon multiplier tube (PMT); and a photonic crystal fiber (PCF).

A pulse compressor can be utilized to pre-compensate the group delay dispersion of femtosecond laser light to provide transform-limited pulses incident on the luminal surface of the vessel being imaged. The imaging catheter can be connected to a photonic crystal fiber (PCF) (e.g., LMA-20, NKT Photonics) of the OCT-TPL imaging system, which can enable single-mode propagation of both OCT light and TPL excitation light and transmission of TPL emission light.

EXAMPLE 4

OCT-TPL Catheter Design and Optical Simulation Using ZEMAX

In this example, the OCT-TPL catheter will modify the current OCT catheter to incorporate the TPL excitation and emission. Previously, detection of macrophages loaded with nanoparticles was performed using a custom-built multiphoton microscope [30]. Therefore, it is desirable to compare the TPL excitation efficacy of the proposed catheter-based OCT-TPL imaging system with the multiphoton microscope. Table 1 shows the characterization of laser excitation from both imaging systems.

TABLE 1

Comparison of the TPL excitation efficacy of a multiphoton microscope with the proposed catheter-based OCT-TPL system.

| Laser Parameter | Multiphoton Microscope | Catheter-based OCT-TPL System |
|---|---|---|
| Wavelength (nm) | 800 | 800 |
| Repetition Rate (MHz) | 76 | 0.5-80 |
| Pulse Width (fs) | 150 | 10-1000 |
| Spot Size (µm) | 0.96 | 10-30 |
| Spot Area (µm$^2$) | 0.72 | 78.5-706.9 |
| Pixel Dwell Time (µs) | 2.5 | 4-20 |
| Number of Pulses per Pixel | 190 | 10-1600 |
| Average Power on Sample (mW) | 20 | 500-2500 |
| False Energy (nJ) | 0.26 | 6-5000 |
| Instantaneous Power (MW) | 1.75E-3 | 0.0625-5 |
| Instantaneous Power Density (MW/µm$^2$) | 1.16E-3 | 2E-4-16E-3 (based on a 20 µm spot size) |

As a PCF will be used to deliver TPL excitation light, the instantaneous power that can be delivered is limited by onset of non-linear effects in the PCF, which can be described using the Nonlinear Schrödinger equation:

$$\frac{\partial A}{\partial z} + \frac{i\beta_2}{2}\frac{\partial^2 A}{\partial t^2} = i\gamma|A|^2 A$$

Where $|A|^2$, $\beta_2$, $\gamma$, z and t are, respectively, pulse instantaneous power [W], group velocity dispersion parameter [fs$^2$ cm$^{-1}$], nonlinear parameter [W$^{-1}$ km$^{-1}$], position [cm] and time [s]. For the PCF used in this example, given that $\gamma=21$ W$^{-1}$ km$^{-1}$ [17], $\beta_2=-172$ fs$^2$ cm$^{-1}$, $\lambda=800$ nm, c=3×10$^8$ m/s, the maximum instantaneous power below the threshold of nonlinear effects in the PCF is solved from the Nonlinear Schrödinger equation: $|A|^2=-2\pi^2 c^2\beta_2/(\lambda^2\gamma)=4.49$ MW. Although the femtosecond laser in OCT-TPL system can provide an instantaneous power of 5 MW (see Table 1), the actual instantaneous power that propagates in the PCF can be limited to approximately 4.49 MW to be less than the threshold of nonlinear effect. Allowance of some non-linearity in the PCF may provide for spectral broadening and additional pulse compression.

Figure 8:
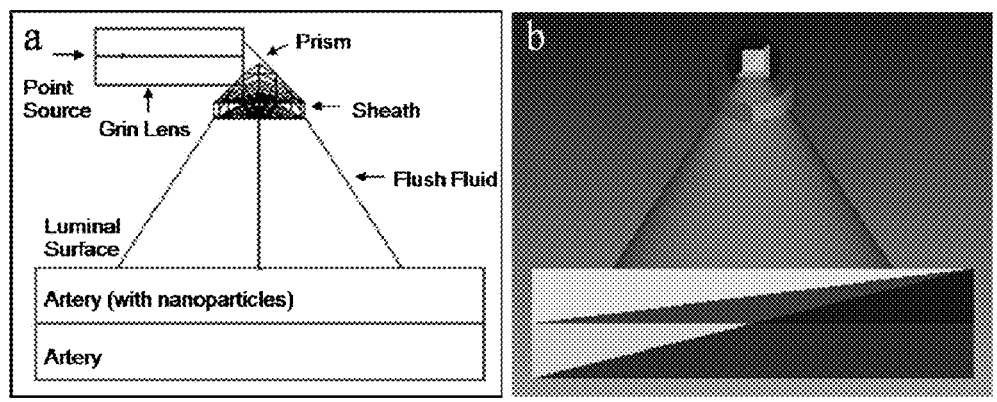
FIG. 8 shows a schematic of an apparatus according to an exemplary embodiment.

ZEMAX is a software program which can model, analyze, and assist in the design of optical systems. Exemplary embodiments of OCT-TPL catheters can be simulated and validated using ZEMAX. A ZEMAX model of the OCT-TPL catheter has been built to simulate OCT and TPL light interaction with arterial tissue containing gold nanoparticles (see e.g. FIG. 8, which provides: (a) a 2-D side-view of OCT-TPL catheter; and (b) 3-D front-view of OCT-TPL catheter).

The catheter is modeled using a grin lens (material: GTAG), a prism (BK7), a sheath (THV_GENERIC) and flush fluid (seawater). Arterial tissue is modeled using a two-layer geometry. Top-layer contains gold nanoparticles ($\mu_a=181$ cm$^{-1}$) and intima ($\mu_s=239$ cm$^{-1}$), while bottom-layer is composed of only intima. The absorption coefficient of intima tissue and scattering coefficient of nanoparticles are ignored since they are negligible compared to those of gold nanoparticles and intima tissue, respectively.

ZEMAX simulation of OCT and TPL light interaction with arterial tissue is performed in three steps: (1) incident OCT (1310 nm) and TPL (800 nm, 1.35 MW, NA=0.04) excitation rays onto arterial tissue from a point source located at the center of the front surface of the grin lens. (2)

a single macrophage cell (containing gold nanoparticles) at the beam-tissue interface is excited and emits TPL. (3) TPL emission rays from the macrophage cell is traced back to the catheter and detected by a detector located at the front surface of the grin lens (not shown in FIG. 6).

Three important parameters are calculated from the ZEMAX simulation, including TPL optical path length (OPL), OCT and TPL emission spot size at the front surface of the grin lens, and TPL emission power at the front surface of the grin lens which can be coupled into the PCF. Specifically, Table 2 shows the OPLs of five different wavelengths of TPL excitation ranging from 798-802 nm both at chief ray and edge ray directions. Results indicate that the dispersion of TPL excitation pulse within the range of 5 nm from the front surface of the grin lens to arterial tissue surface is less than 1 fs.

TABLE 2

Dispersion of TPL excitation light ranging from 798-802 nm both at chief ray and edge ray directions.

| Wavelength (nm) | OPL (mm) Chief Ray ($\theta = 0°$) | OPL (mm) Edge Ray ($\theta = 2.29°$) |
|---|---|---|
| 798 | 4.91664060 | 4.91662242 |
| 799 | 4.91656997 | 4.91655178 |
| 800 | 4.91649954 | 4.91648133 |
| 801 | 4.91642930 | 4.91641106 |
| 802 | 4.91635924 | 4.91634099 |
| Numerical Aperture (NA) | 0.04 | 0.04 |
| $\Delta$OPL ($\mu$m) | 0.281353472 | 0.281426256 |
| Dispersion (fs) | 0.93784 | 0.93809 |

Figure 9:
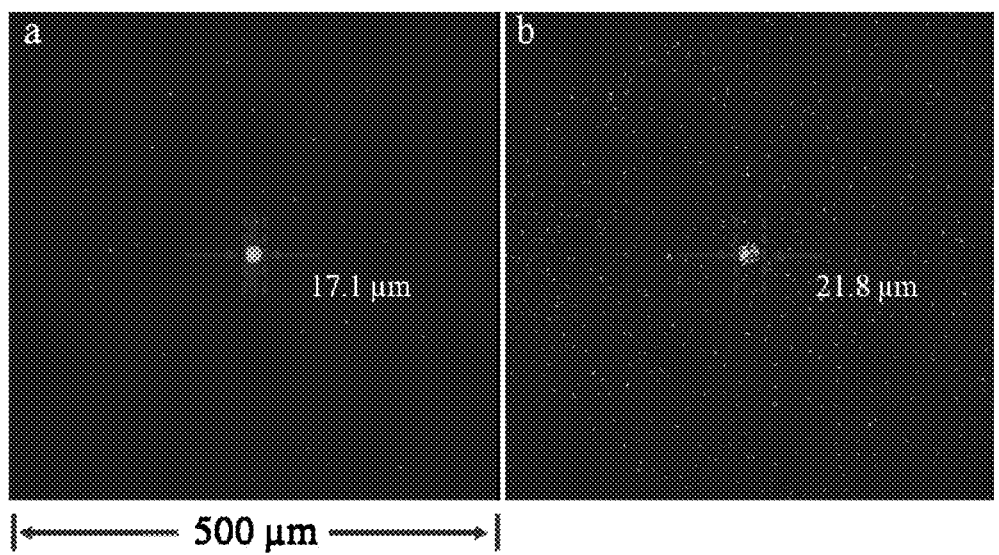
FIG. 9 shows an image obtained from an apparatus according to an exemplary embodiment.

The OCT and TPL spot size at the front surface of the grin lens is measured by a detector located at the same position in ZEMAX (FIG. 9, which shows the OCT and TPL spot size at the front surface of the grin lens measured by a detector located at the same position. The size of the detector is the same as the diameter of the grin lens.) As NA of OCT light (0.05) is higher than TPL excitation (0.04), OCT spot size (17.1 $\mu$m) is slightly smaller than TPL emission spot size (21.8 $\mu$m). The PCF to be used has a core diameter of, for example, 25 $\mu$m, which indicates that both OCT and TPL spot size can be fit into the core.

The TPL emission power that can be coupled into the PCF core is then calculated from the detector shown in FIG. 5, only the rays within the 25 $\mu$m diameter from the center of spot size are included. Based on TPL excitation instantaneous power (1.35 MW), the detected TPL emission instantaneous power at the detector within the 25 $\mu$m diameter is calculated to be $1.51 \times 10^{-4}$ W, which suggests that a single TPL excitation pulse (800 fs) is able to generate 425 photons/pulse. As TPL excitation and OCT repetition rates are, respectively, 500 kHz and 50 kHz, 10 TPL excitation pulsed can be recorded within a single OCT A-scan, which results in 4250 photons/OCT A-scan. In comparison, the multiphoton microscope used to collect data records 0.7 photons/pulse (calculated from the Hamamatsu PMT specifications [31], data not shown) and the accumulated photons/pixel in a typical TPL image of nanoroses from the multiphoton microscope are limited to 133 photons/pixel. Therefore, the detection efficacy of catheter-based OCT-TPL system is more than an order of magnitude higher than the currently used multiphoton microscope.

EXAMPLE 5

Nanorod Selection

Gold nanorods can be internalized by macrophages (an important early cellular marker involved in atherosclerosis and cancer) and used as a contrast agent for a variety of imaging techniques for macrophage targeting. An objective of this study is to compare two-photon luminescence (TPL) properties of four sizes of gold nanorods with surface plasmon resonance at 700, 756, 844 and 1060 nm respectively. TPL from single nanorods and rhodamin 6G particles was measured using a laser-scanning TPL microscope. TPL emission spectrum from nanorods was recorded by a spectrometer with a photon multiplying CCD. All four sizes of nanorods produced strong TPL intensities with a dependence on the excitation wavelength, indicating the two-photon action cross section (TPACS) is plasmon-enhanced. Quadratic dependence of luminescence intensity on excitation power (confirming a TPL process) was observed at low power levels, followed by an intensity saturation or decrease at high power levels due to a photobleaching effect. Largest TPACS of a single nanorod was measured to be 12271 GM compared to 25 GM of a single rhodamin 6G particle at 760 nm excitation. Characteristics of nanorods TPL emission spectrum can be explained by the recombination of electrons near the Fermi level with holes near the X and L symmetry points in the Brillouin zone. Comparison results of TPL brightness, TPACS and emission spectra of nanorods can be used to guide selection of brightest contrast agent for selected imaging applications.

Atherosclerosis, one of the most common cardiovascular diseases, accounts for one-third of all deaths in the United States. [32]. Macrophages in the blood stream infiltrate into the intimal layer of blood vessels containing atherosclerotic plaques and become plaque-based macrophages (PBMs). PBMs accelerate inflammation by releasing matrix metalloproteinases (MMPs) which erode the thin fibrous cap (less than 65 $\mu$m in thickness) and make the plaques more prone to rupture [33, 34]. Tumor-associated macrophages (TAMs) are known to play a fundamental role in the progression of many cancers (e.g., breast, prostate, ovarian, cervical, lung carcinoma and cutaneous melanoma) [35]. In tumors, infiltrated TAMs provide an immunosuppressive microenvironment (through direct and indirect suppression of cytotoxic T cell activity) for tumor growth, promote angiogenesis, and produce soluble mediators that support proliferation and survival of malignant cells [36]. For these reasons, TAM density in solid tumors is generally described as correlating inversely with patient prognosis [35]. Additionally, an association between TAM presence and local invasion into ectopic tissue and/or metastasis has been established in many cancers [35, 36]. Thus, macrophage is an important early cellular marker that provides information relevant to the risk of future plaque rupture and staging and metastasis of cancers. In vivo macrophage detection is of great clinical significance and has motivated development of macrophage-targeting contrast agents such as gold nanoparticles.

A variety of gold nanoparticles with different coatings have been developed to target macrophages due to their unique optical properties (i.e., absorption, scattering and fluorescence), negligible cytotoxicity and good biocompatibility, including nanospheres [37, 38], nanoshells [39, 40], nanocages [41, 42], nanoroses [43, 44], nanorods [45, 46], etc. While the quantum yield of bulk gold fluorescence was observed to be extremely weak (~$10^{-10}$) [47], gold nanoparticles can strongly enhance the local light-field amplitude

[48, 49] and significantly increase the quantum yield to the $10^{-4}$ level [49] by the surface plasmon resonance (SPR) effect [51-53], which is known as coherent oscillation of electrons in the conduction band of the gold nanoparticle in resonance with the incident electromagnetic light-field of light. Due to drastic suppression of interband damping, nanorods exhibit higher local field enhancement factors than small nanospheres [54]. Mohamed et al observed a more than $10^6$ times enhancement of quantum yield of gold nanorods by single photon plasmonic excitation over bulk gold [55]. Nanorods, unlike their counterparts with symmetrical shapes (e.g., nanospheres, nanoshells and nanocages), can easily tune the SPR to near-infrared wavelengths (where tissue absorption is at minimum) by varying the aspect ratios [56-59]. Moreover, the synthesis procedure of nanorods is well established, providing better monodispersity and stability compared to the synthesis of other complex nanostructures (e.g., nanoroses and nanocages). Two-photon or multi-photon excitation processes, better than single-photon excitation, provide additional local field enhancement, and thus, a greater enhancement of quantum yield with stronger emission signals. Although the single-photon quantum yield of a nanorod is in the order of $10^{-4}$, it has been reported that the two-photon action cross section (TPACS) of nanorod can reach 2320 GM, which is within the range of that of quantum dots (2000-47000 GM) [60] and much higher than that of organic fluorophores (e.g., rhodamin 6G), providing a promising approach to detect these nanorods in biological tissues using two-photon excitation.

Two-photon luminescence microscopy (TPLM) is of particular interest because of its near-infrared excitation where tissues scatter more weakly and have less absorption. TPLM can provide best contrast of nanorods and highest 3-D spatial resolution compared to other imaging modalities (e.g., MRI, CT, PET, OCT and ultrasound) [61-63]. Several TPLM studies of single nanorods have been reported with detailed description of quadratic power dependence [64, 65], local field enhancement at specific positions of nanorod [65], luminescence polarization and spectrum [60, 67]. However, further characterization and comparison of two-photon luminescence (TPL) from nanorods of different sizes at multiple excitation wavelengths is needed, these include: (1) comparison of TPL brightness of nanorods, (2) range excitation power of TPL process and photobleaching effect of nanorods, (3) TPACS of nanorods, and (4) TPL spectra of nanorods. These studies can provide a deeper understanding of TPL from nanorods and guide contrast agent selection and optimization.

In this study, a laser-scanning TPL microscope was used to investigate the TPL characterization of nanorods of different sizes at multiple excitation wavelengths. Nanorods with plasmon-resonance at 756 nm were found to be the brightest (at same excitation power) among all four sizes of nanorods at 760 nm excitation. All nanorods exhibit a quadratic dependence of TPL intensity on excitation power at low power levels, followed by an intensity saturation or decrease at high power levels due to a photobleaching effect. TPACS of four nanorods at three excitation wavelengths was calculated and compared. TPL emission spectra of nanorods was interpreted by electron-hole recombination and is consistent with TPL brightness measurement. Results of these experiments and analysis suggest that nanorod size determines not only SPR position but also TPL brightness, TPACS and TPL emission spectrum.

Materials and Methods

Sample Preparation

Figure 10:
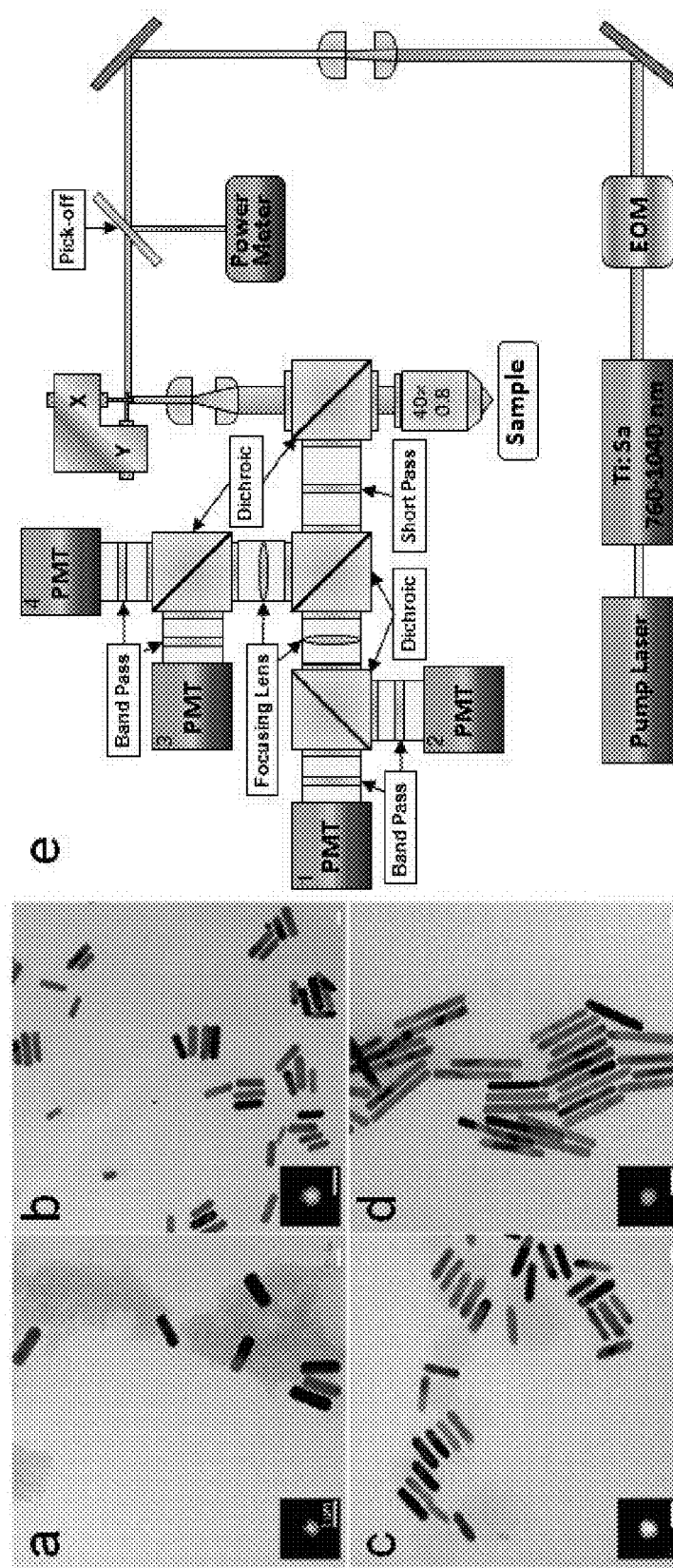
FIG. 10 shows a schematic of an apparatus according to an exemplary embodiment.

Gold nanorods were synthesized in solution using a seeded growth method as described previously [68]. Four sizes of nanorods with surface plasmon resonance at 700, 756, 844 and 1060 nm respectively were purchased from Nanopartz, briefly sonicated and diluted 10 times from stock concentration before use. Nanorod samples were prepared by dispersing 5 μl dilution onto a glass slide and covered by a coverslip, forming a 5 μm thick nanorod solution. Final concentration of four sizes of nanorods on the glass slide are, respectively, $5.7 \times 10^{10}$, $4 \times 10^{10}$, $7.2 \times 10^{10}$ and $2.8 \times 10^{10}$ nanoparticles/ml. Transmission electron microscopy (TEM) revealed morphologies of nanorods and TPL images showed the shapes of a single nanorod at the diffraction limit (FIG. 10a-d). FIG. 10 provides TEM images of gold nanorods used in the study: (a) Au700, (b) Au756, (c) Au844, (d) Au1060. Insets in (a,b,c,d) are TPL images of a single nanorod at 840 nm excitation within the spectral range of 400-700 nm. Scale bars in TEM and TPL images represent 20 nm and 1 μm, respectively. (e) Schematic diagram of the laser scanning TPL microscope. EOM: electro-optic modulator; PMT: photomultiplier tube.

The long axis of the gold nanorods are in the range of 35-67 nm, with corresponding aspect ratios of 2.9, 3.5, 4.4 and 6.7, respectively. Rhodamin 6G (Sigma-Aldrich, St. Louis, Mo.) was diluted into two concentrations in DI water: 110 μM and 1 pM. Sample with 110 μM was sealed into a cuvette, while sample with 1 pM was dispersed and then dried on a glass slide (forming a distribution of single rhodamin 6G particles). TPACS spectrum was measured for both cuvette and dried rhodamin 6G samples.

TPL Microscopy

TPL from nanorods was measured using a laser scanning TPL microscope (FIG. 10b, Prairie Technologies, Middleton, Wis.). A femtosecond Ti:Sapphire laser (Mai Tai HP, Newport, Irvine, Calif.) emitting at 760-1040 nm (80 MHz, 100 fs) was used as an excitation light source. Intensity of the laser beam entering the microscope was modulated by an electro-optic modulator (350-80, ConOptics, Danbury, Conn.) and monitored by a pick-off mirror (reflectance 1%) with a power meter for measuring the power delivered to the sample. The focal volume of the objective lens (40×, NA=0.8, water emersion, Olympus, Center Valley, Pa.) was scanned over the sample in the x-y plane using a pair of galvanometric scanning mirrors to produce 2-D images. TPL emission from sample was collected through the same objective, separated from the excitation laser line by a 720 nm long-pass dichroic mirror, directed into four channels and detected by four photomultiplier tubes (PMT1,2: H7422P-40, PMT3,4: R3896, Hamamatsu, Bridgewater, N.J.) in spectral ranges of 640-680, 570-620, 490-560 and 435-485 nm, respectively. To minimize the photon count from excitation laser line, a short-pass filter (et720sp, Chroma Technology, Bellows Falls, Vt.) was placed after the dichroic mirror. In this study, only PMT1 was used to collect TPL emission signals (less than 720 nm) with absence of dichroic mirrors and a band-pass filter in detection light path. The TPL was also measured by replacing PMT1 with a fiber-coupled spectrometer with a photon multiplying CCD (Shamrock 303i, Andor Technology, Belfast, Ireland).

TPACS Calculation

TPACS of nanorods were determined by a comparison method of the TPL emission from the reference rhodamin 6G sample. TPL emission from a sample can be expressed in Eq. (1) with related parameters [69]:

$$F \frac{1}{2} \phi C \eta_2 \sigma_2 \frac{g_p}{f\tau} \frac{8nP^2}{\pi\lambda} \quad (1)$$

Where F (in photons/second) is the TPL photons collected per unit time, $\phi$ (dimensionless) is the TPL collection efficiency of the measurement system, C (in mol/ml) is the fluorophore concentration (i.e., nanorod and rhodamin 6G), $g_p$ (dimensionless) is the degree of second-order temporal coherence of the excitation source, f is the laser modulation frequency, $\tau$ is the FWHM pulse width, n is the refractive index of the sample, P (in photons/second) is the excitation laser power, $\lambda$ is the excitation wavelength, $\eta_2\sigma_2$ (in GM; $1GM=10^{-50}$ $cm^4s/photon$) is the TPACS where $\eta_2$ and $\sigma_2$ are quantum yield and two-photon absorption cross section respectively. By measuring the TPL emission intensity from single particles in TPL images, $F_n$ (nanorod) and $F_r$ (rhodamin 6G) were obtained. Here, all TPL signals were measured under identical excitation wavelength with the same experimental conditions in the same system, therefore, $\phi$, $g_p$, $f$, $\tau$ and $\lambda$ are the same for nanorod and rhodamin 6G samples. Using Eq. (1) for two samples and change P to average power $\overline{P}$ (in Watts), TPACS of nanorod $((\eta_2\sigma_2)_n)$ can be determined by comparing with the known TPACS of rhodamin 6G $((\eta_2\sigma_2)_r)$ as shown in Eq. (2):

$$(\eta_2\sigma_2)_n = \frac{n_r}{n_n} \cdot \frac{\overline{P}_r^2}{\overline{P}_n^2} \cdot \frac{F_n}{F_r} \cdot (\eta_2\sigma_2)_r \quad (2)$$

Results

Power Dependence of Nanorod Brightness

Figure 11:
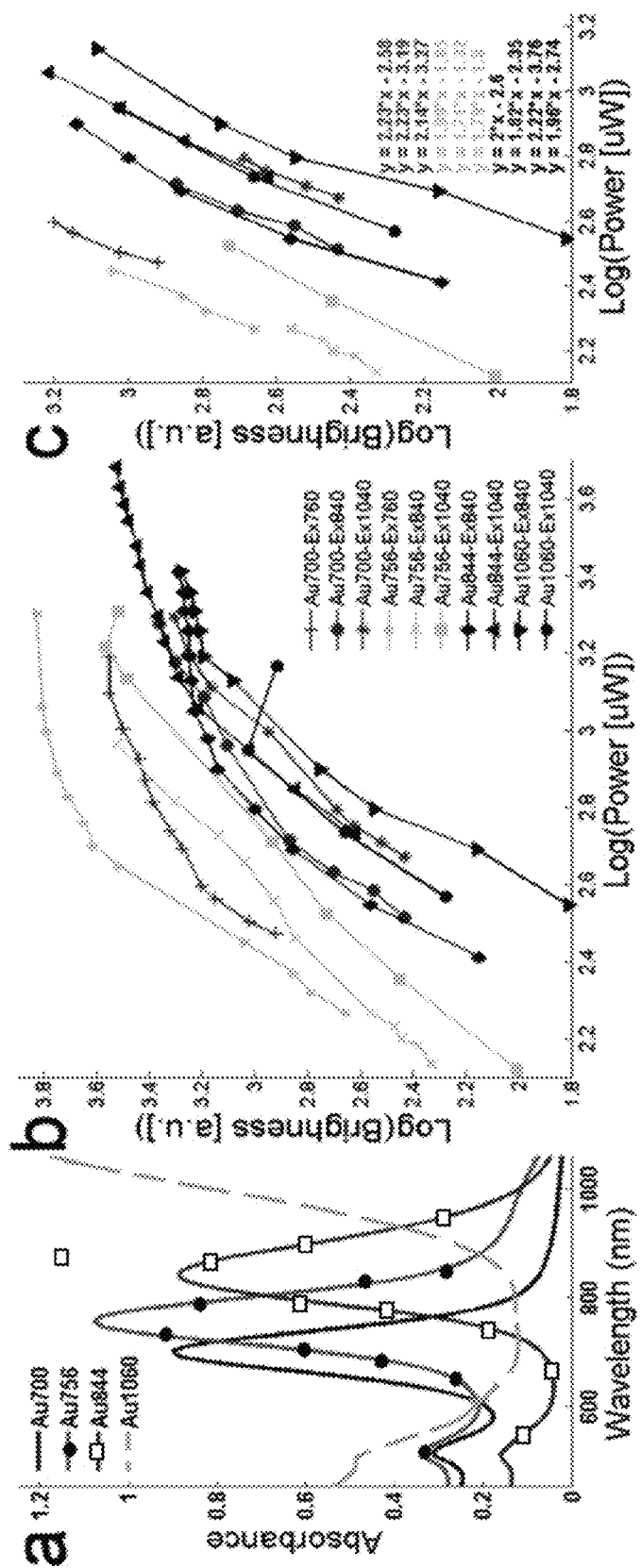
FIG. 11 shows data obtained from an apparatus according to an exemplary embodiment.

FIG. 11a shows single-photon absorbance spectra of four sizes of nanorods measured at a concentration of $4\times10^{11}$ nanoparticles/ml. FIG. 11b shows MPL intensity dependence on the excitation laser power (132 µW-4.8 mW) of nanorods at wavelengths of 760, 840 and 1040 nm. FIG. 11c shows quadratic dependence of luminescence intensity of nanorods on excitation laser power at lower power levels in (b). Slopes of 1.7-2.2 (for each size of nanorod at different excitation wavelength) confirm the TPL process.

For each nanorod, two surface plasmon resonance (SPR) absorption peaks are visible, one at around 520 nm is due to transverse oscillation of electrons and insensitive to the size of nanorods. The other absorption peak is red-shifted to longer wavelengths and is due to longitudinal oscillation of electrons with a peak wavelength that increases with nanorod aspect ratio [55,69]. Amplitude of longitudinal SPR also increases with aspect ratio (except for Au844), consistent with theoretical calculations [56]. Multi-photon luminescence (MPL) of four sizes of nanorods at three excitation wavelengths (i.e., 760, 840, 1060 nm) was measured by the TPL microscope. FIG. 11b shows nanorod brightness dependence on the excitation laser power (132 µW-4.8 mW) in logarithmic scale. MPL signal intensity is observed to first linearly increase (i.e., slope≈2) at lower excitation powers for each nanorod, then the curve starts to bend and form an exponential-like increase followed by signal saturation (e.g., Au700-Ex760,840,1040; Au756-Ex760; Au844-Ex840, 1060; Au1060-Ex840) or signal decrease (Au760-Ex1040, Au1060-Ex1040). At the same excitation power, MPL signal intensity is higher when excitation wavelength is closer to the longitudinal SPR of the nanorod. When the excitation is at (or close to) the longitudinal SPR wavelength, MPL signal intensity (i.e., nanorod brightness) is observed to follow: Au756>Au700>Au844>Au1060, where Au756 appears 11 times brighter than Au1060 at the excitation power of 372 µW. FIG. 11c shows nanorod MPL at lower excitation power levels of FIG. 11b. Slopes of all curves ranging from 1.7-2.2 show a quadratic dependence of luminescence signal intensity on the laser excitation power, indicating a TPL process. Of note is that the TPL process power range varies with nanorod size, where bigger nanorods (e.g., Au844, Au1060) appear to have wider power ranges than smaller nanorods (e.g., Au700, Au756).

MPL response as a function of time was measured to test MPL photobleaching properties of nanorods. Nanorods in a smaller field of view (20×20 µm²) were irradiated at 2 mW for 30 s and a TPL image was recorded by immediately zooming out to a larger field of view (80×80 µm²) as shown in FIG. 12a where the red box indicates the smaller field of view. For each excitation wavelength, the averaged intensity of nanorods in the red box was normalized to that of the nanorods outside the red box in the larger field of view and results were shown in FIG. 11b. While all sizes of nanorods in the red box showed a MPL signal drop after 30 s laser irradiation compared to those in the larger field of view where nanorods experienced a much shorter irradiation time, it was observed that larger sizes of nanorods (i.e., Au844, Au1060) showed a more drastic signal drop (e.g., 35% drop for Au1060 at 1040 nm excitation) at longitudinal SPR excitation wavelength compared to smaller nanorods (e.g., 2% drop for Au756 at 760 nm excitation). MPL temporal response of nanorods suggest that a photobleaching effect is evident, especially in larger sizes of nanorods.

FIG. 12a shows a typical TPL image (80×80 µm2) of Au1060 at 844 nm excitation acquired after 30 s laser irradiation at 2 mW in the red box (20×20 µm2) in (a) where a MPL signal drop of nanorods is observed. FIG. 12b shows averaged MPL signal of nanorods in the red box (second bar of the same color) was normalized to that of the nanorods outside the red box in the larger field of view (first bar of the same color) for four sizes of nanorods at three excitation wavelengths. Error bar represents standard deviation.

TPACS Measurement of Nanorods

TPACS of rhodamin 6G needs to be measured before that of nanorods can be determined. TPACS of rhodamin 6G solution with an excitation wavelength range of 690-960 nm has been reported by Albota et al [71], however, this data does not include wavelength range of 960-1040 nm. In this study, we measured and calculated the normalized TPACS of both rhodamin 6G solution and single particle using Eq. (1) at excitation wavelength range of 760-1040 nm extending Albota et al data by 80 nm. A TPL process of rhodamin 6G was observed at all excitation wavelengths and applied power range (data not shown). Measurement of rhodamin 6G solution reasonablely matches reported values in 760-960 nm range with the major absorption peak overlapped at 820 nm. The absorption peak of a single rhodamin particle has a blue shift to 800 nm and the second peak at 1000 nm is drastically attenuated compared to rhodamin 6G solution. TPACS of a single rhodamin 6G particle was then used as a brightness reference for comparison with nanorods in accordance with Eq. (2).

TPL signals of nanorods were measured at less than 1 mW excitation power where a TPL process can be warranted. The TPL brightness of a single nanorod was then compared with that of a single rhodamin 6G particle using Eq. (2) and results are shown in Table 3. We observe that (1) All nanorods have largest TPACS at or close to the longitudinal SPR wavelength, consistent with previous measurement on gold nanorods with longitudinal SPR at 820 nm [60].

TPACS decreases monotonically with excitation wavelength departing from the longitudinal SPR; (2) Smaller nanorods have larger TPACS than bigger nanorods with excitation wavelength at or close to the longitudinal SPR (e.g., Ex760 for Au 756 and Au700 compared to Ex840 for Au844 and Ex1040 for Au1060). The TPACS of Au756 at 760 nm excitation is largest (12271 GM compared to 25 GM of a single rhodamin 6G particle) among all nanorods and excitation wavelengths investigated and about 15 times larger than that of Au1060 at 1040 nm excitation. The TPACS of Au844 at 840 nm excitation is 2039 GM, which is very close to 2320 GM reported previously for a slightly bigger size of nanorods excited at 830 nm [60].

Figure 13:
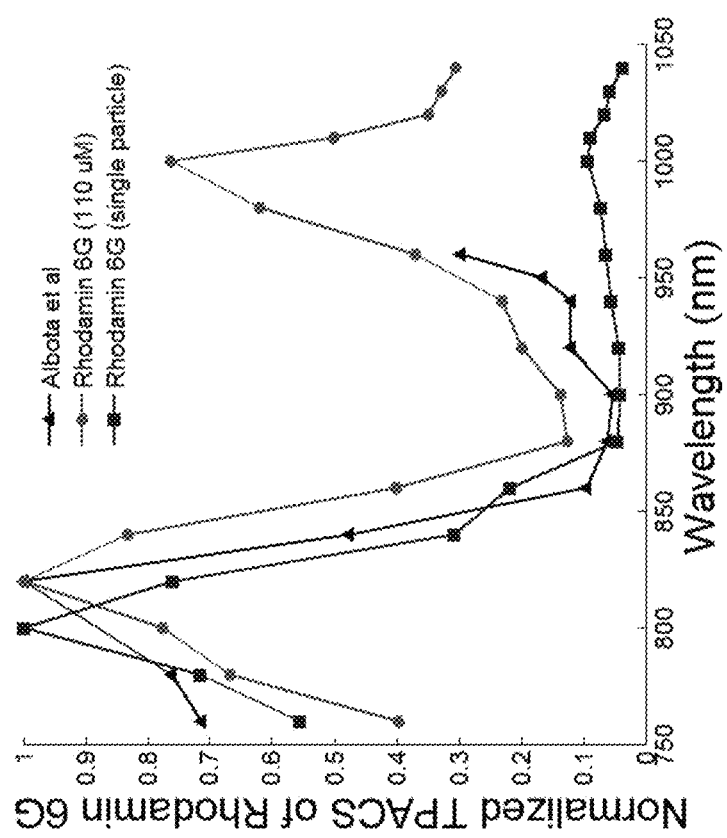
FIG. 13 shows data obtained from an apparatus according to an exemplary embodiment.

FIG. 13 shows normalized TPACS of rhodamin 6G single particle, rhodamin 6G solution and reported values from Albota et al [41] at wavelength range of 760-1040 nm. Single rhodamin 6G particles were formed from dried water solution; Rhodamin 6G solution has a concentration of 110 µM dissolved in DI water; Reported data used a rhodamin 6G concentration of 110 µM dissolved in MeOH.

TABLE 3

TPACS (in GM units) of single nanorod at excitation wavelengths of 760, 840 and 1040 nm respectively.

|  | Au700 | Au756 | Au844 | AU1060 |
| --- | --- | --- | --- | --- |
| Ex760 | 9802 | 12271 |  |  |
| Ex840 | 2194 | 8412 | 2039 | 474 |
| Ex1040 | 632 | 2391 | 671 | 682 |

3.3 TPL Emission Spectra of Nanorods

To better characterize the TPL emission of nanorods, TPL emission spectra were collected from a nanorod solution (80×80 µm$^2$ field of view) in the spectral range of 350-700 nm at multiple excitation wavelengths (i.e., 760, 800, 840 and 1040 nm). The average excitation power on all nanorods was kept less than 1 mW so that a TPL process can be satisfied. TPL emission was then normalized by the number of incident photons and nanorod concentration and shown in FIG. 14.

FIG. 14 shows TPL emission spectra of (a) Au700, (b) Au756, (c) Au844 and (d) Au1060 at the excitation wavelengths of 760, 800, 840 and 1040 nm. Inset in (a) represents total quantum efficiency of the detection system including the electron multiplying CCD and gratings of the spectrometer. Spectra was corrected for the quantum efficiency and normalized on the number of incident photons and nanorod concentration All TPL spectra were corrected for the total quantum efficiency of the photon multiplying CCD and gratings of the spectrometer (inset in FIG. 14a). For each nanorod size, TPL emission intensity appears highest at nanorod's longitudinal SPR wavelength and decreases monotonically with excitation wavelengths departing from the longitudinal SPR peak, suggesting the electric-field enhancement due to SPR absorption. The further the excitation wavelength shifts away from the SPR, the more drastically TPL emission signal drops, which is consistent with the results of PMT measurement of nanorod brightness as shown in FIG. 11b. All emission spectral intensities increase for lower photon energies where the excitation wavelength is located (except for Au1060 at 1040 nm excitation), which can be attributed to the dispersion of the localized SPR [72]. The emission spectral range can be separated into three wavelength bands: 400-575, 575-640 and 640-700 nm. Two dips at around 575 and 640 nm are visible in the spectra of all sizes of nanorods, and more evident for Au756, Au844 and Au1060. For smaller nanorods (i.e., Au700, Au756), TPL emission intensity in the 640-700 nm band increases more rapidly than the other two bands compared to bigger nanorods (i.e., Au844). Interestingly, TPL emission of Au1060 exhibits a plateau in the 400-575 nm band followed by a signal decrease in 575-640 and 640-700 nm bands. Because the TPL mechanism for gold nanorods is the same as that for bulk gold metal [72], the emission peak regions should be attributed to the energy gap between the excited electrons at the Fermi level and the holes in the d-band. We note that the second harmonic signals are also observed for nanorods at 1040 nm excitation, and not seen at all other excitation wavelengths. Details of the spectral features are discussed below.

Discussion

As nanorod brightness is very important parameter in macrophage targeting and detection, and also determines the sensitivity of an imaging system, selecting the size of nanorod that yields strongest TPL signals is of great clinical interest and significance. In this study, four sizes of nanorods were compared and Au756 was found to emit strongest at the same excitation power and at the excitation wavelength of corresponding longitudinal SPR. In fact, fluorescence emission by single photon excitation from gold nanorods is determined by three factors as demonstrated by Eustis and El-Sayed in their experimental and simulation studies [73]: (1) The strength of single-photon absorbance at longitudinal SPR wavelength, which should increase with increasing nanorod aspect ratio (FIG. 11a). (2) The overlap between the SPR absorption band and the interband transition which is attributed to the electron transition between the d-band and conduction band, and started at the threshold energy around 1.8 eV (689 nm) [74, 75]. (3) The overlap between the SPR absorption band and the fluorescence band of bulk gold which peaks around 525 nm, decreases thereafter and diminishes beyond 750 nm [47]. The first factor is a competing component to the other two factors, the net effect of which determines the enhancement of TPL emission. In this study, as the aspect ratio of nanorods increases from 2.9 to 6.7, enhancement of longitudinal SPR increases while the overlap between the SPR absorption band and interband transition or bulk fluorescence of gold both decreases. Therefore, the observed strongest enhancement results in Au756 with an aspect ratio of 3.5, which is about 12 times higher than Au1060. This observation is very similar to that reported for nanorods with single-photon excitation, where quantum yield of nanorods increases quadratically for aspect ratios below 3.4 and decreases afterwards [76], and fluorescence emission starts to decline as aspect ratios increase beyond 3.25 to about an order of magnitude weaker with aspect ratio at 6 [73].

Figure 12:
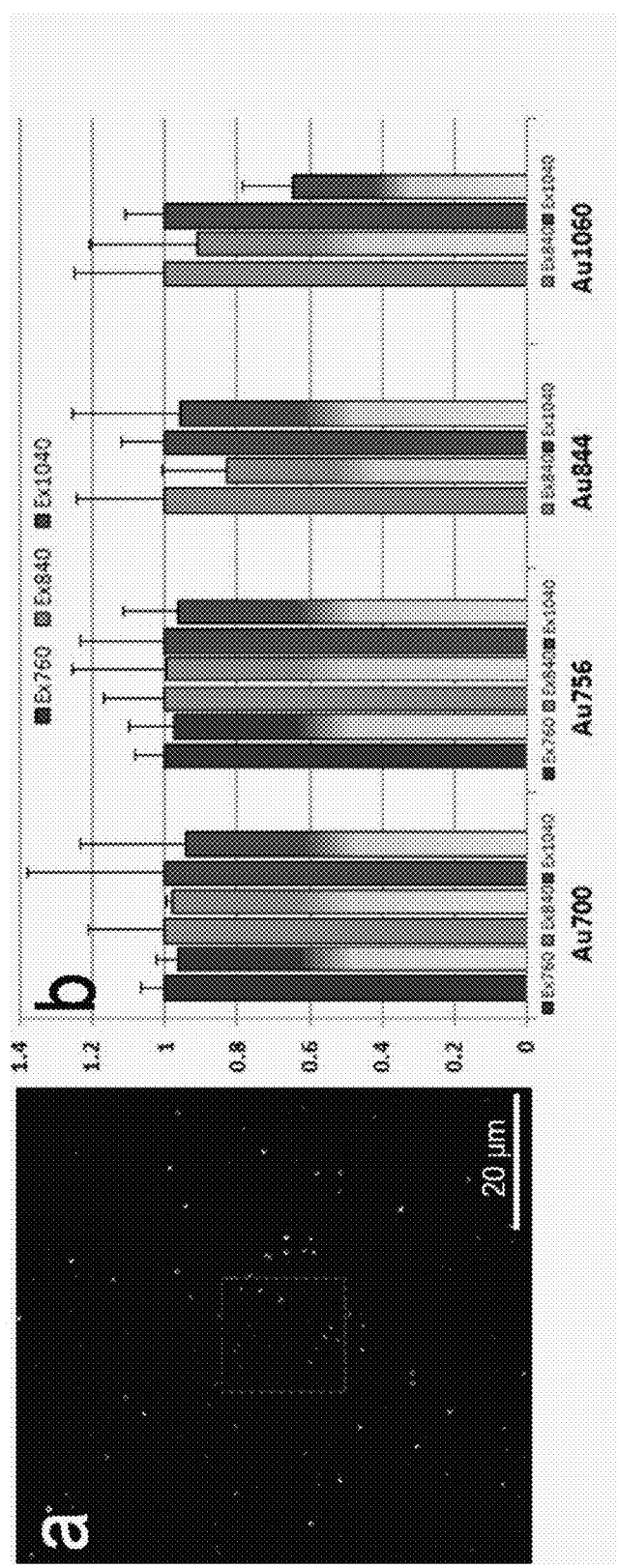
FIG. 12 shows data obtained from an apparatus according to an exemplary embodiment.

Unlike single-photon excitation where nanorods are essentially inert to photobleaching and light scattering on nanorods can stay constant for several hours of measurement time in contrast to fluorescence from quantum dots or dyes [77], TPL emission signal from nanorods exhibits various levels of photobleaching depending on the size of nanorods (FIG. 12). In fact, TPL emission is determined by instantaneous incident power. TPL emission signal first increases when increasing excitation power due to the enhancement of emission by incident field, then decreases and eventually diminishes due to vanishing of the enhancement by nanorod shape transformation or damage. Link and El-Sayed et al [78] demonstrated that the threshold for complete melting of the nanorods is about 0.01 J/cm$^2$ (100 GW/cm$^2$) with a pulse duration of 100 fs at 800 nm excitation, while an apparent shape transformation of nanorods and a decrease of longitudinal SPR band is observed at 10 GW/cm$^2$. Bouhelier et al [79] has shown that nanorods can be transformed to spherical shape at high excitation powers and the corresponding luminescence peak is blue-shifted, where emission enhancement can be greatly reduced. In this study, instantaneous power density at the beam focus was 13 GW/cm$^2$ (average power of 2 mW) at 1040 nm excitation, which is more than 10 GW/cm$^2$ and very likely to reshape part of the nanorods in the field of view. Therefore, it is expected that luminescence emission will be reduced and, moreover, this photobleaching effect is attributed to reshaping or partial nanorod damage, especially for those with a bigger size (i.e., Au844, Au1060) and aligned with polarization of incident laser light.

Gold crystal structure is known to have several symmetry points in the first Brillouin zone with electron transitions preferentially occurring near the X and L symmetry points [67, 80]. In gold nanorods, X and L symmetry points can be along the directions of the long axis and diagonal of nanorod, respectively [67]. The TPL emission process in nanorods can be interpreted in three steps [46,54,74]: (1) Electrons in occupied d-band (or possibly sp-conduction-band below the Fermi level [67]) are excited by two-photon absorption to unoccupied sp-conduction-band above the Fermi level and electron-hole pairs are created. (2) Excited electrons then lose energy (e.g., through intraband scattering) to move energetically closer to the Fermi level. (3) Recombination of the electron-hole pairs result in luminescent emission. According to band structure calculation of gold [72, 81], emission peak regions should be in the spectral ranges of 1.8-1.9 eV (652-689 nm), 2.3-2.4 eV (517-539 nm) and 3.1-3.3 eV (376-400 nm), which are attributed to the symmetry points of 6-5X, 6-5L and 6-4L, respectively. In this study, the TPL emission peaks of nanorods at corresponding longitudinal SPR excitation wavelengths are all observed to locate at around 680 nm and 530 nm, and a sharp rising edge presents at around 400 nm, which is very consistent with the band calculations of emissions from 6-5X, 6-5L and 6-4L symmetry points respectively. Worth noting is that second harmonic signals are evident only at 1040 nm excitation (consistent with the reported observation [71]) but not observed at other excitation wavelengths, which may result from the immersion of the weak second harmonic signals in the dispersion of the TPL emissions.

CONCLUSION

By utilizing TPLM, TPL properties of gold nanorods were investigated and characterized. Four sizes of nanorods with longitudinal SPR wavelengths of 700, 756, 844 and 1060 nm were excited at multiple excitation wavelengths (i.e., 760, 840, 1040 nm). Au756 was observed to emit strongest TPL signal at 760 nm excitation with the same excitation power among all nanorods. Quadratic dependence of TPL intensity on excitation power was satisfied at low power levels (e.g., <1.6 mW), while a photobleaching effect was evident especially for larger-sized nanorods at a high power level (e.g., >1.6 mW). TPACS of nanorods at three excitation wavelengths was calculated based on the measurement of normalized TPACS spectrum of a single rhodamin 6G particle. TPL emission spectra of nanorods match the electron band calculations of gold and is consistent with TPL brightness measurement. Results suggest that gold nanorods are a promising imaging contrast agent for TPLM, and brightest nanorods can be determined by comparison of TPL brightness, TPACS and emission spectra of nanorods.

All of the devices, systems and/or methods disclosed and claimed herein can be made and executed without undue experimentation in light of the present disclosure. While the devices, systems and methods of this invention have been described in terms of particular embodiments, it will be apparent to those of skill in the art that variations may be applied to the devices, systems and/or methods in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

REFERENCES

The contents of the following references are incorporated by reference herein:
[1] Yusuf S, Reddy S, Ounpuu S, Anand S, "Global burden of cardiovascular diseases: part I: general considerations, the epidemiologic transition, risk factors, and impact of urbanization," Circulation 104, 2746-2753 (2001)
[2] Libby P, Ridker P M, Maseri A, "Inflammation and Atherosclerosis," Circulation 105, 1135-1143 (2002)
[3] Libby P, Theroux P, "Pathophysiology of coronary artery disease," Circulation 111, 3481-8 (2005)
[4] Lucas A R, Korol R, Pepine C J, "Inflammation in atherosclerosis: some thoughts about acute coronary syndromes," Circulation 113, e728-732 (2006)
[5] Virmani R, Burke A P, Kolodgie F D, Farb A, "Pathology of the Thin-Cap Fibroatheroma: A Type of Vulnerable Plaque," J Intery Cardiol 16(3), 267-272 (2003)
[6] Davies M J, Richardson P D, Woolf N, Katz D R, Mann J, "Risk of thrombosis in human atherosclerotic plaques: role of extracellular lipid, macrophage, and smooth muscle cell content," Br Heart J 69, 377-381 (1993)
[7] Stary H C, Chandler A B, Dinsmore R E, "A definition of advanced types of atherosclerotic lesions and a histological classification of atherosclerosis: a report from the Committee on Vascular Lesions of the Council on Arteriosclerosis," Circulation 92, 1355-1374 (1995)
[8] Jonasson L, Holm J, Skalli O, Bondjers G, Hansson G K, "Regional accumulations of T cells, macrophages, and smooth muscle cells in the human atherosclerotic plaque," Arteriosclerosis 6, 131-138 (1986)
[9] Johnson J L, George S J, Newby A C, Jackson C L, "Divergent effects of matrix metalloproteinases 3, 7, 9, and 12 on atherosclerotic plaque stability in mouse brachiocephalic arteries," Proc Natl Acad Sci 102, 15575-15580 (2005)
[10] Henney A M, Wakeley P R, Davies M J, Foster K, Hembry R, Murphy G, Humphries S, "Localization of stromelysin gene expression in atherosclerotic plaques by in situ hybridization," Proc Natl Acad Sci 88, 8154-8158 (1991)
[11] Galis Z S, Sukhova G K, Lark M W, Libby P, "Increased expression of matrix metalloproteinases and matrix degrading activity in vulnerable regions of human atherosclerotic plaques," J Clin Invest 94, 2493-2503 (1994)
[12] Nikkari S T, O'Brien K D, Ferguson M, Hatsukami T, Welgus H G, Alpers C E, Clowes A W, "Interstitial collagenase (MMP-1) expression in human carotid atherosclerosis," Circulation 92, 1393-1398 (1995)
[13] Libby P, Geng Y J, Aikawa M, Schoenbeck U, Mach F, Clinton S K, Sukhova G K, Lee, R T, "Macrophages and atherosclerotic plaque stability," Curr Opin Lipidol 7, 330-335 (1996)

[14] Taubman M B, Fallon J T, Schecter A D, Giesen P, Mendlowitz M, Fyfe B S, Marmur J D, Nemerson Y, "Tissue factor in the pathogenesis of atherosclerosis," Thromb Haemost 78, 200-204 (1997)

[15] Kolodgie F D, Virmani R, Burke A P, Farb A, Weber D K, Kutys R, Finn A V, Gold H K, "Pathologic assessment of the vulnerable human coronary plaque," Heart 90, 1385-1391 (2004)

[16] van Zandvoort M, Engels W, Douma K, Beckers L, Oude Egbrink M, Daemen M, Slaaf D W, "Two-photon microscopy for imaging of the (atherosclerotic) vascular wall: a proof of concept study," J Vasc Res 41, 54-63 (2004)

[17] Zoumi A, Lu X A, Kassab G S, Tromberg B J, "Imaging coronary artery microstructure using secondharmonic and two-photon fluorescence microscopy," Biophys J 87, 2778-2786 (2004)

[18] Boulesteix T, Pena A M, Pages N, Godeau G, Sauviat M P, Beaurepaire E, Schanne-Klein M C, "Micrometer scale ex vivo multiphoton imaging of unstained arterial wall structure," Cytometry Part A 69A, 20-26 (2006)

[19] Le T T, Langohr I M, Locker M J, Sturek M, Cheng J X, "Label-free molecular imaging of atherosclerotic lesions using multimodal nonlinear optical microscopy," J Biomed Opt 12(5), 0540071-05400710 (2007)

[20] Lilledahl M B, Haugen O A, de Lange Davies C, Svaasand L O, "Characterization of vulnerable plaques by multiphoton microscopy," J Biomed Opt 12(4), 0440051-04400512 (2007)

[21] Wang T, Mancuso J J, Sapozhnikova V, Dwelle J, Ma L L, Willsey B, Kazmi S M, Qiu J, Li X, Asmis R, Johnston K P, Feldman M D, Milner T E, "Dual-wavelength multi-frequency photothermal wave imaging combined with OCT for macrophage and lipid detection in atherosclerotic plaques", J Biomed Opt 17(3), 0360091-03600910 (2012)

[22] Wang T, Mancuso J J, Kazmi S M, Dwelle J, Sapozhnikova V, Willsey B, Ma L L, Qiu J, Li X, Dunn A K, Johnston K P, Feldman M D, Milner T E, "Combined two-photon luminescence microscopy and OCT for macrophage detection in the hypercholesterolemic rabbit aorta using plasmonic gold nanorose", Lasers Surg Med 44(1), 49-59 (2012)

[23] Xue P, Fujimoto J G, "Ultrahigh resolution optical coherence tomography with femtosecond Ti:sapphire laser and photonic crystal fiber," Chinese Science Bulletin 53(13), 1963-1966 (2008)

[24] Ryu S Y, Choi H Y, Na J H, Choi E S, Yang G H, Lee B H, "Optical coherence comography implemented by photonic crystal fiber," Opt Quant Electron 37(13-15), 1191-1198 (2005)

[25] Fu L, Gu M, "Double-clad photonic crystal fiber coupler for compact nonlinear optical microscopy imaging," Opt Lett 31, 1471-1473 (2006)

[26] Liu G, Kieu K, Wise F W, Chen Z, "Multiphoton microscopy system with a compact fiber-based femtosecond-pulse laser and handheld probe," J Biophoton 4, 34-39 (2011).

[27] Fu L, Jain A, Xie H, Cranfield C, Gu M, "Nonlinear optical endoscopy based on a double-clad photonic crystal fiber and a MEMS mirror," Opt Exp 14, 1027-1032 (2006)

[28] Wu Y, Xi J, Cobb M J, Li X, "Scanning fiber-optic nonlinear endomicroscopy with miniature aspherical compound lens and multimode fiber collector," Opt Lett 34, 953-955 (2009)

[29] Kim, E H, Dave, D P, Milner, T E. "Fiber-optic spectral polarimeter using a broadband swept laser source," Optics Communications, 249 351-356 (2005)

[30] Park J, Estrada A, Sharp K, Sang K, Schwartz J A, Smith D K, Coleman C, Payne J D, Korgel B A, Dunn A K, Tunnell J W, "Two-photon-induced photoluminescence imaging of tumors using near-infrared excited gold nanoshells," Opt Exp 16(3), 1590-1599 (2008)

[31] Available at http://sales.hamamatsu.com/assets/pdf/parts_H/m-h7422e.pdf

[32] V. L. Roger, A. S. Go, D. M. Lloyd-Jone, R. J. Adams, J. D. Berry, T. M. Brown, M. R. Carnethon, S. Dai, G. de Simone, E. S. Ford, C. S Fox, H. J. Fullerton, C. Gillespie, K. J. Greenlund, S. M. Hailpern, J. A. Heit, P. M. Ho, V. J. Howard, B. M. Kissela, S. J. Kittner, D. T. Lackland, J. H. Lichtman, L. D. Lisabeth, D. M. Makuc, G. M. Marcus, A. Marelli, D. B. Matchar, M. M. McDermott, J. B. Meigs, C. S. Moy, D. Mozaffarian, M. E. Mussolino, G. Nichol, N. P. Paynter, W. D. Rosamond, P. D. Sorlie, R. S. Stafford, T. N. Turan, M. B. Turner, N. D. Wong and J. Wylie-Rosett, "Heart disease and stroke statistics—2011 update: a report from the American Heart Association," Circulation 123(4), e18-e209 (2011).

[33] E. Falk, P. K. Shah and V. Fuster, "Coronary plaque disruption," Circulation 92(3), 657-671 (1995).

[34] F. D. Kolodgie, R. Virmani, A. P. Burke, A. Farb, D. K. Weber, R. Kutys, A. V. Finn and H. K. Gold, "Pathologic assessment of the vulnerable human coronary plaque," Heart 90(12), 1385-1391 (2004).

[35] N. B. Hao, M. H. Lu, Y. H. Fan, Y. L Cao, Z. R. Zhang, and S. M. Yang, "Macrophages in tumor microenvironments and the progression of tumors," Clin. Dev. Immunol. 2012, 948098-948108 (2012).

[36] B. Ruffell, N. I. Affara, and L. M. Coussens. "Differential macrophage programming in the tumor microenvironment," Trends Immunol. 33(3), 119-126 (2012).

[37] R. Shukla, V. Bansal, M. Chaudhary, A. Basu, R. R. Bhonde, and M. Sastry, "Biocompatibility of gold nanoparticles and their endocytotic fate inside the cellular compartment: a microscopic overview," Langmuir 21(23), 10644-10654 (2005).

[38] M. M. Janát-Amsbury, A. Ray, C. M. Peterson, and H. Ghandehari, "Geometry and surface characteristics of gold nanoparticles influence their biodistribution and uptake by macrophages," Eur. J. Pharm. Biopharm. 77(3), 417-423 (2011).

[39] S. Lal, S. E. Clare, and N. J. Halas, "Nanoshell-enabled photothermal cancer therapy: impending clinical impact," Acc. Chem. Res. 41(12), 1842-1851 (2008).

[40] X. Ji, R. Shao, A. M. Elliott, R. J. Stafford, E. Esparza-Coss, G. Liang, X. P. Luo, K. Park, J. T. Markert, and C. Li, "Bifunctional Gold Nanoshells with a Superparamagnetic Iron Oxide-Silica Core Suitable for Both MR Imaging and Photothermal Therapy," J. Phys. Chem. C 111 (17), 6245-6251 (2007).

[41] S. E. Skrabalak, L. Au, X. Lu, X. Li, and Y. Xia, "Gold nanocages for cancer detection and treatment," Nanomedicine (Lond) 2(5), 657-668 (2007).

[42] M. Longmire, P. L. Choyke, and H. Kobayashi, "Clearance properties of nano-sized particles and molecules as imaging agents: considerations and caveats," Nanomedicine (Lond) 3(5), 703-717 (2008).

[43] L. L. Ma, M. D. Feldman, J. M. Tam, A. S. Paranjape, K. K. Cheruku, T. A. Larson, J. O. Tam, D. R. Ingram, V. Paramita, J. W. Villard, J. T. Jenkins, T. Wang, G. D. Clarke, R. Asmis, K. Sokolov, B. Chandrasekar, T. E. Milner, and K. P. Johnston, "Small multifunctional nanoclusters (nanoroses) for targeted cellular imaging and therapy," ACS Nano 3(9), 2686-2696 (2009).

[44] T. Wang, J. J. Mancuso, S. M. Kazmi, J. Dwelle, V. Sapozhnikova, B. Willsey, L. L. Ma, J. Qiu, X. Li, A. K. Dunn, K. P. Johnston, M. D. Feldman, and T. E. Milner, "Combined two-photon luminescence microscopy and OCT for macrophage detection in the hypercholesterolemic rabbit aorta using plasmonic gold nanorose," Lasers Surg. Med. 44(1), 49-59 (2012).

[45] T. S. Hauck, A. A. Ghazani, and W. C. W. Chan, "Assessing the effect of surface chemistry on gold nanorod uptake, toxicity, and gene expression in mammalian cells," Small 4(1), 153-159 (2008).

[46] T. Niidome, M. Yamagata, Y. Okamoto, Y. Akiyama, H. Takahashi, T. Kawano, Y. Katayama, and Y. Niidome, "PEG-modified gold nanorods with a stealth character for in vivo applications," J. Control Release 114(3), 343-347 (2006).

[47] A. Mooradian, "Photoluminescence of metals," Phys. Rev. Lett. 22(5), 185-187 (1969).

[48] J. Zheng, C. Zhang, and R. M. Dickson, "Highly fluorescent, water-soluble, size-tunable gold quantum dots," Phys. Rev. Lett. 93(7), 077402-077405 (2004).

[49] G. Wang, T. Huang, R. W. Murray, L. Menard, and R. G. Nuzzo, "Near-IR luminescence of monolayer-protected metal clusters," J. Am. Chem. Soc. 127(3), 812-813 (2005).

[50] J. P. Wilcoxon, J. E. Martin, F. Parsapour, B. Wiedenman, and D. F. Kelley, "Photoluminescence from nanosize gold clusters," J. Chem. Phys. 108(21), 9137-9143 (1998).

[51] Y. Fang, W. Chang, B. Willingham, P. Swanglap, S. Dominguez-Medina, and S. Link, "Plasmon emission quantum yield of single gold nanorods as a function of aspect ratio," ACS Nano 6(8), 7177-7184 (2012).

[52] P. K. Jain, X. Huang, I. H. El-Sayed, and M. A. El-Sayed, "Review of some interesting surface plasmon resonance-enhanced properties of noble metal nanoparticles and their applications to biosystems," Plasmonics 2(3), 107-118 (2007).

[53] M. A. El-Sayed, "Some interesting properties of metals confined in time and nanometer space of different shapes," Acc. Chem. Res. 34(4), 257-264 (2001).

[54] C. Sönnichsen, T. Franzl, T. Wilk, G. von Plessen, J. Feldmann, O. Wilson, and P. Mulvaney, "Drastic reduction of plasmon damping in gold nanorods," Phys. Rev. Lett. 88, 077402-077405 (2002).

[55] M. B. Mohamed, V. Volkov, S. Link, and M. A. El-Sayed, "The 'lightning' gold nanorods: fluorescence enhancement of over a million compared to the gold metal," Chem. Phys. Lett. 317(6), 517-523 (2000).

[56] S. Link, M. B. Mohamed, and M. A. El-Sayed, "Simulation of the optical absorption spectra of gold nanorods as a function of their aspect ratio and the effect of the medium dielectric constant," J. Phys. Chem. B 106(16), 3073-3077 (1999).

[57] S. S. Verma and J. S. Sekhon, "Influence of aspect ratio and surrounding medium on localized surface plasmon resonance (LSPR) of gold nanorod," J. Optics 41(2), 89-93 (2012).

[58] P. K. Jain, X. Huang, I. H. El-Sayed and M. A. El-Sayed, "Noble metals on the nanoscale: optical and photothermal properties and some applications in imaging, sensing, biology, and medicine," Acc. Chem. Res. 41(12), 1578-1586 (2008).

[59] E. T. Castellana, R. C. Gamez, M. E. Gómez, and D. H. Russell, "Longitudinal surface plasmon resonance based gold nanorod biosensors for mass spectrometry," Langmuir 26(8), 6066-6070 (2010).

[60] H. Wang, T. B. Huff, D. A. Zweifel, W. He, P. S. Low, A. Wei, and J. X. Cheng, "In vitro and in vivo two-photon luminescence imaging of single gold nanorods," Proc. Natl. Acad. Sci. USA 102(44), 15752-15756 (2005).

[61] L. Tong, Q. Wei, A. Wei, and J. X. Cheng, "Gold nanorods as contrast agents for biological imaging: optical properties, surface conjugation and photothermal effects," Photochem. Photobiol. 85(1), 21-32 (2009).

[62] T. Y. Ohulchanskyy, I. Roy, K. T. Yong, H. E. Pudavar, and R. N. Prasad, "High-resolution light microscopy using luminescent nanoparticles," WIREs Nanomed. Nanobiotechnol. 2(2), 162-175 (2010).

[63] D. Nagesha, G. S. Laevsky, P. Lampton, R. Banyal, C. Warner, C. DiMarzio, and S. Sridhar, "In vitro imaging of embryonic stem cells using multiphoton luminescence of gold nanoparticles," Int. J. Nanomedicine 2(4), 813-819 (2007).

[64] Y. Zhang, J. Yu, D. J. S. Birch, and Y. Chen, "Gold nanorods for fluorescence lifetime imaging in biology," J. Biomed. Opt. 15(2), 0205041-0205043 (2010).

[65] C. L. Chen, L. R. Kuo, C. L. Chang, Y. K. Hwu, C. K. Huang, S. Y. Lee, K. Chen, S. J. Lin, J. D. Huang, and Y. Y. Chen, "In situ real-time investigation of cancer cell photothermolysis mediated by excited gold nanorod surface plasmons," Biomaterials 31(14), 4104-4112 (2010).

[66] H. Okamoto and K. Imura, "Near-field imaging of optical field and plasmon wavefunctions in metal nanoparticles," J. Mater. Chem. 16(40), 3920-3928 (2006).

[67] K. Imura, T. Nagahara, and H. Okamoto, "Near-field two-photon-induced photoluminescence from single gold nanorods and imaging of plasmon modes," J. Phys. Chem. B 109(27), 13214-13220 (2005).

[68] W. H. Ni, X. S. Kou, Z. Yang, and J. F. Wang, "Tailoring longitudinal surface plasmon wavelengths, scattering and absorption cross sections of gold nanorods," ACS Nano 2(4), 677-686 (2008).

[69] C. Xu and W. W. Webb, "Measurement of two-photon excitation cross sections of molecular fluorophores with data from 690 to 1050 nm," JOSA B 13(3), 481-491 (1996).

[70] R. Gans, "Form of ultramicroscopic particles of silver," Ann. Phys. 47(10), 270-284 (1915).

[71] M. A. Albota, C. Xu, and W. W. Webb, "Two-photon fluorescence excitation cross sections of biomolecular probes from 690 to 960 nm," Appl. Opt. 37(31), 7352-7356 (1998).

[72] G. T. Boyd, Z. H. Yu, and Y. R. Shen, "Photoinduced luminescence from the noble metals and its enhancement on roughened surfaces," Phys. Rev. B 33(12), 7923-7936 (1986).

[73] S. Eustis and M. A. El-Sayed, "Aspect ratio dependence of the enhanced fluorescence intensity of gold nanorods: experimental and simulation study," J. Phys. Chem. B 109(34), 16350-16356 (2005).

[74] M. Guerrisi and R. Rosei, "Splitting of the interband absorption edge in Au", Phys. Rev. B 12(2), 557-563 (1975).

[75] X. Huang, S. Neretina, and M. A. El-Sayed, "Gold nanorods: from synthesis and properties to biological and biomedical applications," Adv. Mater. 21(48), 4880-4910 (2009).

[76] K. S. Lee and M. A. El-Sayed, "Dependence of the enhanced optical scattering efficiency relative to that of absorption for gold metal nanorods on aspect ratio, size, end-cap shape and medium refractive index," J. Phys. Chem. B 109(43), 20331-20338 (2005).

[77] C. Sönnichsen and A. P. Alivisatos, "Gold nanorods as novel nonbleaching plasmon-based orientation sensors for polarized single-particle microscopy," Nano Lett. 5(2), 301-304 (2005).

[78] S. Link, C. Burda, B. Nikoobakht, and M. A. El-Sayed, "Laser-induced shape changes of colloidal gold nanorods using femtosecond and nanosecond laser pulses" J. Phys. Chem. B 104(26), 6152-6163 (2000).

[79] A. Bouhelier, R. Bachelot, G. Lerondel, S. Kostcheev, P. Royer, G. P. Wiederrecht, "Surface plasmon characteristics of tunable photoluminescence in single gold nanorods," Phys. Rev. Lett. 95(26), 2674051-2674054 (2005).

[80] R. E. Hummel, *Electronic Properties of Materials*, 37-61, 4th ed. (Springer, New York, 2011).

[81] R. Rosei, and P. Winsemius, "Splitting of the interband absorption edge in Au," Phys. Rev. B 12(2), 557-563 (1975).

The invention claimed is:

1. An apparatus comprising:
   an optical coherence tomography light source configured to emit a first wavelength;
   a splitter configured to direct the first wavelength emitted from the coherence tomography light source to a reference path and to a sample path;
   a short-pulsed light source configured to emit a second wavelength;
   a first dichroic element;
   a second dichroic element; and
   a photonic crystal fiber, wherein the photonic crystal fiber is configured to simultaneously:
      enable single-mode propagation of the first wavelength from the optical coherence tomography light source to a sample site;
      enable single-mode propagation of the second wavelength from the short-pulsed light source to the sample site;
      transmit an optical coherence tomography signal from the sample site, wherein the optical coherence tomography signal is generated from the first wavelength; and
      transmit an emission signal from the sample site, wherein the emission signal is induced by the second wavelength from the short-pulsed light source.

2. The apparatus of claim 1 wherein the optical coherence tomography light source is configured as a swept source optical coherence tomography light source.

3. The apparatus of claim 1 wherein the optical coherence tomography light source is configured as a broadband optical coherence tomography light source.

4. The apparatus of claim 1 wherein the photonic crystal fiber is configured to allow single mode transmission of light emitted from the optical tomography light source and configured to allow single mode transmission of light emitted from the short-pulsed light source.

5. The apparatus of claim 1 further comprising a balanced detector.

6. The apparatus of claim 5 wherein the balanced detector is configured to minimize a non-interfering OCT component.

7. The apparatus of claim 1 further comprising a photon counting detector.

8. The apparatus of claim 7 wherein the photon counting detector is a photomultiplier tube.

9. The apparatus of claim 7 wherein the photon counting detector is an avalanche photo diode.

10. The apparatus of claim 7 wherein the photon counting detector is configured to detect two-photon luminescence.

11. The apparatus of claim 1 wherein the second dichroic element is configured to direct two photon luminescence toward a photon counting detector.

12. The apparatus of claim 1 wherein the first dichroic element is configured to direct the first and second wavelengths to the sample path.

13. The apparatus of claim 1 wherein the sample path is directed to a sample site that comprises nanoparticles.

14. The apparatus of claim 1 further comprising a visual display configured to display an image of the sample site.

15. The apparatus of claim 14 wherein the visual display is configured to enhance a portion of the display of the sample site based on the distance between the apparatus and the sample site.

16. The apparatus of claim 15 wherein the visual display is configured to increase the brightness of a location of the sample site where a detected value exceeds a normalized value.

17. The apparatus of claim 13 wherein the nanoparticles are configured as nanorods.

18. The apparatus of claim 17 wherein the nanorods comprise gold and have a surface plasmon resonance of approximately 756 nm.

19. The apparatus of claim 1 further comprising a dispersion compensating element.

20. The apparatus of claim 19 wherein the dispersion compensating element is configured to compensate dispersion differences of light emitted from the optical coherence tomography light source between the reference path and the sample path.

21. The apparatus of claim 19 wherein the dispersion compensating element is configured to pre-compensate two-photon luminescence excitation light.

22. The apparatus of claim 1 wherein the short-pulsed light source is a short-pulsed laser having a pulse energy between 10 pJ and 1 mJ and pulse duration between 5 fs and 100 ps.

* * * * *